(12) United States Patent
Collinson et al.

(10) Patent No.: US 11,642,448 B2
(45) Date of Patent: May 9, 2023

(54) MULTIPLE DRESSING NEGATIVE PRESSURE WOUND THERAPY SYSTEM WITH CALIBRATED LEAK PATHS

(71) Applicant: Smith & Nephew PLC, Watford (GB)

(72) Inventors: Sarah Jenny Collinson, Hull (GB); Edward Yerbury Hartwell, Hull (GB); Felix Clarence Quintanar, Hull (GB)

(73) Assignee: Smith & Nephew PLC, Watford (GB)

( * ) Notice: Subject to any disclaimer, the term of this patent is extended or adjusted under 35 U.S.C. 154(b) by 167 days.

(21) Appl. No.: 16/494,224

(22) PCT Filed: Mar. 15, 2018

(86) PCT No.: PCT/EP2018/056494
§ 371 (c)(1),
(2) Date: Sep. 13, 2019

(87) PCT Pub. No.: WO2018/167199
PCT Pub. Date: Sep. 20, 2018

(65) Prior Publication Data
US 2021/0187171 A1     Jun. 24, 2021

Related U.S. Application Data

(60) Provisional application No. 62/471,595, filed on Mar. 15, 2017.

(51) Int. Cl.
*A61M 1/00*     (2006.01)
*A61F 13/02*    (2006.01)

(52) U.S. Cl.
CPC .......... *A61M 1/75* (2021.05); *A61F 13/0216* (2013.01); *A61M 1/74* (2021.05); *A61M 1/912* (2021.05);
(Continued)

(58) Field of Classification Search
CPC ................. A61M 1/962; A61M 1/74; A61M 2205/3334; A61M 2205/502; A61M 1/90;
(Continued)

(56) References Cited

U.S. PATENT DOCUMENTS 7,438,705 B2   10/2008   Karpowicz et al.
8,974,429 B2    3/2015   Gordon et al.
(Continued)

FOREIGN PATENT DOCUMENTS

EP           3295971 A1      3/2018
WO   WO-2013071253 A1        5/2013
(Continued)

OTHER PUBLICATIONS

International Preliminary Report on Patentability for Application No. PCT/EP2018/056494, dated Sep. 26, 2019, 10 pages.
(Continued)

*Primary Examiner* — Kai H Weng
*Assistant Examiner* — Brandon W. Levy
(74) *Attorney, Agent, or Firm* — Knobbe, Martens Olson & Bear LLP

(57) ABSTRACT

In some embodiments, an apparatus for providing negative pressure wound therapy to multiple wounds includes a negative pressure source configured to couple via a plurality of fluid flow paths to a plurality of wound dressings. The plurality of flow paths includes a plurality of calibrated leaks. The apparatus also includes a controller configured to determine a total rate of flow in the plurality of fluid flow paths and compare the total rate of flow to a plurality of thresholds associated with the plurality of calibrated leaks to determine one or more operating conditions, such as a blockage in one or more of the plurality of flow paths. An indication of the operating condition can be provided.

15 Claims, 15 Drawing Sheets

(52) U.S. Cl.
CPC ............ *A61M 1/918* (2021.05); *A61M 1/962* (2021.05); *A61M 1/982* (2021.05); *A61M 2205/3334* (2013.01); *A61M 2205/502* (2013.01)

(58) Field of Classification Search
CPC ................ A61M 1/75; A61M 2205/15; A61M 2205/84; A61M 2209/088; A61M 1/732; A61M 2205/3365; A61H 9/0057; A61F 13/0216; A61F 2013/0054; A61F 2013/00536
See application file for complete search history.

(56) References Cited

U.S. PATENT DOCUMENTS

| | | | | |
|---|---|---|---|---|
| 10,342,564 | B2* | 7/2019 | Mark | ............... A61B 17/32002 |
| 2007/0219532 | A1* | 9/2007 | Karpowicz | ............. A61M 1/74 604/540 |
| 2012/0123358 | A1 | 5/2012 | Hall et al. | |
| 2013/0131616 | A1* | 5/2013 | Locke | ..................... A61M 1/74 604/319 |
| 2013/0144227 | A1* | 6/2013 | Locke | ..................... A61M 1/98 604/319 |
| 2015/0032031 | A1* | 1/2015 | Hartwell | .................. A61M 1/90 600/587 |
| 2015/0231021 | A1* | 8/2015 | Smith | ................. A61M 1/0003 601/7 |
| 2018/0168916 | A1* | 6/2018 | Kelch | ..................... A61M 1/90 |
| 2020/0054804 | A1* | 2/2020 | Nilsson | ................... A61M 1/86 |
| 2020/0069850 | A1 | 3/2020 | Beadle et al. | |

FOREIGN PATENT DOCUMENTS

| | | | | |
|---|---|---|---|---|
| WO | WO 2016/018448 | | 2/2016 | |
| WO | WO-2016018448 | A1 * | 2/2016 | ....... A61F 13/00068 |

OTHER PUBLICATIONS

International Search Report and Written Opinion, re PCT Application No. PCT/EP2018/056494, dated Jun. 5, 2018.

* cited by examiner

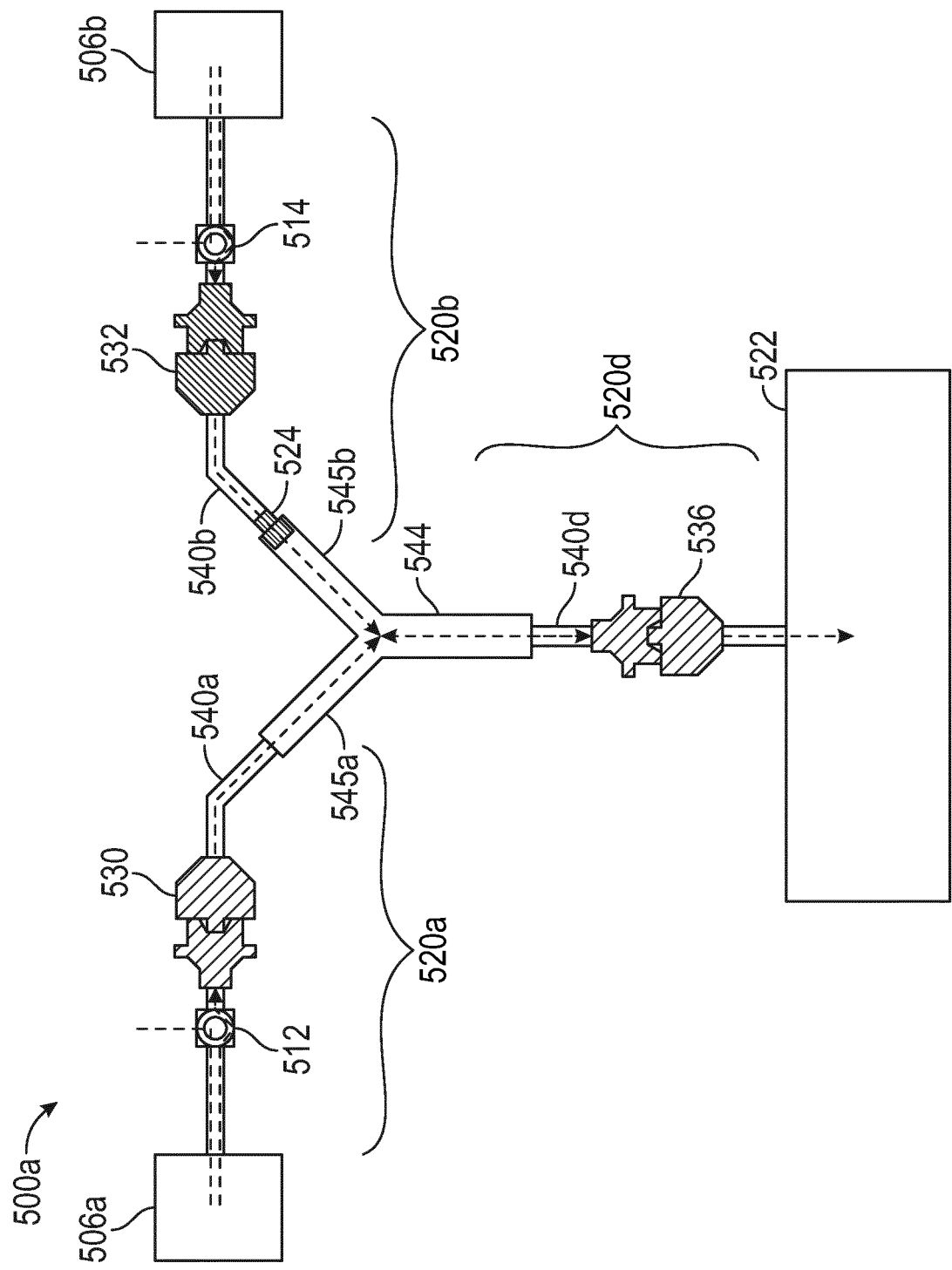

MULTIPLE DRESSING NEGATIVE PRESSURE WOUND THERAPY SYSTEM WITH CALIBRATED LEAK PATHS

RELATED APPLICATIONS

This application is a U.S. national stage application of International Patent Application No. PCT/EP2018/056494, filed Mar. 15, 2018, which claims priority to U.S. Provisional Application No. 62/471,595, filed Mar. 15, 2017, entitled "MULTIPLE DRESSING NEGATIVE PRESSURE WOUND THERAPY SYSTEM WITH CALIBRATED LEAK PATHS," each of which is hereby incorporated by reference in its entirety.

FIELD

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and methods of using TNP systems.

BACKGROUND

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema, encouraging blood flow, stimulating the formation of granulation tissue, removing excess exudates and may reduce bacterial load and, thus, infection to the wound. Furthermore, TNP therapy permits less outside disturbance of the wound and promotes more rapid healing.

SUMMARY

In some embodiments, a negative pressure would therapy apparatus includes a negative pressure source and a controller. The negative pressure source is configured to couple via a plurality of fluid flow paths to a plurality of wound dressings and provide negative pressure to the plurality of wound dressings. The plurality of fluid flow paths include a first fluid flow path and a second fluid flow path. The first fluid flow path is configured to fluidically connect a first wound dressing to a first inlet configured to be in fluid communication with the negative pressure source. The first fluid flow path includes a first fluid leak configured to admit fluid into the first fluid flow path. The second fluid flow path is configured to fluidically connect a second wound dressing to a second inlet configured to be in fluid communication with the negative pressure source. The second fluid flow path includes a second fluid leak configured to admit fluid into the second fluid flow path. The flow of fluid admitted into the second fluid flow path via the second fluid leak is different than a flow of fluid admitted into the first fluid flow path via the first fluid leak. The controller is configured to operate the negative pressure source. The controller is also configured to (i) determine a total rate of flow in the plurality of fluid flow paths, (ii) detect presence of at least one operating condition based at least in part on the determined total rate of flow and at least one of a flow of fluid due to the first fluid leak or a flow of fluid due to the second fluid leak; and (iii) provide indication of the operating condition.

The apparatus of the preceding paragraph may also include any combination of the following features described in this paragraph, among others described herein. The at least one operating condition can include one or more of a blockage condition, a system blocked condition, or a normal operation condition. In some examples, the controller is further configured to (i) based at least in part on a determination that the total rate of flow does not satisfy any of first, second, or third flow thresholds, provide an indication that the system block condition exists or an indication that the blockage condition exists in each of the plurality of fluid flow paths; (ii) based at least in part on a determination that the total rate of flow satisfies the first flow threshold and does not satisfy the second threshold, provide an indication that the blockage condition exists in the second fluid flow path; (iii) based at least in part on a determination that the total rate of flow satisfies the second flow threshold and does not satisfy the third threshold, provide an indication that the blockage condition exists in the first fluid flow path; or (iv) based at least in part on a determination that the total rate of flow satisfies the third flow threshold, provide an indication that the normal operation condition exists. The third flow threshold can correspond to a higher flow than the first and second flow thresholds and the second flow threshold can correspond to higher flow than the first flow threshold.

The apparatus of any of the preceding paragraphs may also include any combination of the following features described in this paragraph, among others described herein. In some examples, the first flow threshold corresponds to an expected first rate of flow in the first fluid flow path. In some examples, the second flow threshold corresponds to an expected second rate of flow in the second fluid flow path. In some examples, the third flow threshold corresponds to an aggregation of the expected first rate of flow in the first fluid flow path and the expected second rate of flow in the second fluid flow path.

The apparatus of any of the preceding paragraphs may also include any combination of the following features described in this paragraph, among others described herein. In some examples, the expected first rate of flow corresponds to the rate of flow in the first fluid path under the normal operation condition. In some examples, the expected second rate of flow corresponds to the rate of flow in the second fluid path under the normal operation condition.

The apparatus of any of the preceding paragraphs may also include any combination of the following features described in this paragraph, among others described herein. In some examples, the first fluid leak modifies a first rate of flow in the fluid flow path such that the expected first rate of flow is different from an expected second rate of flow in the second fluid flow path by more than a threshold amount. In some examples, the controller is further configured to provide on the display a graphical representation of the rate of flow in at least one of the plurality of fluid flow paths. In some examples, the graphical representation of the rate of flow in the fluid flow path includes a gauge.

The apparatus of any of the preceding paragraphs may also include any combination of the following features described in this paragraph, among others described herein. The negative pressure source further includes a vacuum pump including a motor. The controller is further configured to determine the rate of flow in the fluid flow paths by measuring a speed of the motor. The apparatus further includes a tachometer configured to measure the speed of the motor. The controller is further configured to measure a first plurality of motor speeds during a first period of time and to average the first plurality of motor speeds. In some examples, the average of the motor speeds indicative of the total rate of flow. The apparatus further includes a canister configured to collect fluid aspirated from the one or more wounds.

The apparatus of any of the preceding paragraphs may also include any combination of the following features described in this paragraph, among others described herein. The apparatus further includes a device configured to connect the negative pressure source to the plurality of fluid flow paths. The device includes a plurality of dressing conduit attachment portions fluidically connected to a negative pressure attachment portion via a joint. The plurality of dressing conduit attachment portions includes a first dressing conduit attachment portion and a second dressing conduit attachment portion. The first dressing conduit attachment portion includes a first shaft extending away from the joint and the first inlet distal the joint. The first inlet is configured to fluidically connect the first fluid flow path to the negative pressure source. The second dressing conduit attachment portion includes a second shaft extending away from the joint and the second inlet distal the joint. The second inlet is configured to fluidically connect the second fluid flow path to the negative pressure source. The negative pressure attachment portion includes a third shaft extending away from the joint and a third inlet distal the joint. The third inlet is configured to fluidically connect to the negative pressure source.

The apparatus of any of the preceding paragraphs may also include any combination of the following features described in this paragraph, among others described herein. The apparatus further includes a third fluid flow path configured to fluidically connect a third wound dressing to a fourth inlet configured to be in fluid communication with the negative pressure source. The third fluid flow path includes a third fluid leak configured to admit fluid into the third fluid flow path. The flow of fluid admitted into the third fluid flow path via the third fluid leak is different from each flow of fluid admitted into the first and second fluid flow paths via the first and second fluid leaks.

The apparatus of the preceding paragraph may also include any combination of the following features described in this paragraph, among others described herein. The plurality of dressing conduit attachment portions further includes a third dressing conduit attachment portion including a fourth shaft extending away from the joint and the fourth inlet distal the joint. The fourth inlet is configured to fluidically connect the third fluid flow path to the negative pressure source. The controller is further configured to generate one or more graphical user interfaces (GUIs) as described herein.

A method of operating the apparatus of any of the preceding paragraphs may also include any combination of the foregoing features, among others described herein.

In some embodiments, a method of operating a negative pressure wound therapy apparatus includes determining a total rate of flow in a plurality of fluid flow paths configured to fluidically couple a negative pressure source to a plurality of wound dressings configured to be placed over a plurality of wounds. The total rate of flow corresponds to an aggregation of a plurality of rates of flow associated with the plurality of fluid flow paths. The plurality of fluid flow paths includes at least a first fluid flow path configured to fluidically connect a first wound dressing with the negative pressure source and a second fluid flow path configured to fluidically connect a second wound dressing with the negative pressure source. The method further includes, in response to monitoring the total rate of flow, providing an indication of at least one operating condition. The indication at least one operating condition can include providing at least one of an indication that a canister full condition exists or an indication that a blockage condition exists in each of the plurality of fluid flow paths in response to determining that the total rate of flow does not satisfy any of first, second, or third flow thresholds. The indication at least one operating condition can include providing an indication that the blockage condition exists in the second fluid flow path in response to determining that the total rate of flow satisfies the first flow threshold and does not satisfy the second flow threshold. The indication at least one operating condition can include providing an indication that the blockage condition exists in the first fluid flow path in response to determining that the total rate of flow satisfies the second flow threshold and does not satisfy the third flow threshold. The indication at least one operating condition can include providing an indication that a normal operation condition exists in response to determining that the total rate of flow satisfies the third flow threshold. The third flow threshold can correspond to higher flow than the first and second flow thresholds and the second flow threshold can correspond to higher flow than the first flow threshold. The method can be performed by a controller of the negative pressure wound therapy apparatus.

The method of the preceding paragraph may also include any combination of the following features described in this paragraph, among others described herein. The first flow threshold corresponds to an expected first rate of flow in the first fluid flow path The second flow threshold corresponds to an expected second rate of flow in the second fluid flow path. The third flow threshold corresponds to an aggregation of the expected first rate of flow in the first fluid flow path and the expected second rate of flow in the second fluid flow path.

The method of any of the preceding paragraphs may also include any combination of the following features described in this paragraph, among others described herein. The expected first rate of flow corresponds to the rate of flow in the first fluid path under the normal operation condition. The expected second rate of flow corresponds to the rate of flow in the second fluid path under the normal operation condition.

The method of any of the preceding paragraphs may also include any combination of the following features described in this paragraph, among others described herein. The method further includes determining the total rate of flow by measuring a speed of a motor operating the negative pressure source. In some examples, measuring the speed of the motor can include measuring a first plurality of motor speeds during a first period of time and averaging the first plurality of motor speeds, the average being indicative of the rate of flow.

In some embodiments, a method of operating a negative pressure wound therapy apparatus includes determining a total rate of flow in a plurality of fluid flow paths configured to fluidically couple a negative pressure source to a plurality of wound dressings configured to be placed over a plurality of wounds. The total rate of flow corresponds to an aggregation of a plurality of rates of flow associated with the plurality of fluid flow paths. The plurality of fluid flow paths includes at least a first fluid flow path configured to fluidically connect a first wound dressing with the negative pressure source, a second fluid flow path configured to fluidically connect a second wound dressing with the negative pressure source, and a third fluid flow path configured to fluidically connect a third wound dressing with the negative pressure source. The method further includes, in response to monitoring the total rate of flow, providing an indication of at least one operating condition. The indication can be provided by providing at least one of an indication that a canister full condition exists or an indication that the blockage condition exists in each of the plurality of fluid flow paths in response to determining that the total rate of flow does not satisfy any of first, second, third, fourth, fifth, sixth, seventh, or eighth flow thresholds. The indication can be provided by providing an indication that the blockage condition exists in the second fluid flow path and the third fluid flow path in response to determining that the total rate of flow satisfies the first flow threshold and does not satisfy the second flow threshold. The indication can be provided by providing an indication that an abnormal condition exists in response to determining (a) that the total rate of flow satisfies the second flow threshold and does not satisfy the third threshold, or (b) that the total rate of flow satisfies the seventh flow threshold and does not satisfy the eighth flow threshold. The indication can be provided by providing an indication that the blockage condition exists in the first fluid flow path and the third fluid flow path in response to determining that the total rate of flow satisfies the third flow threshold and does not satisfy the fourth flow threshold. The indication can be provided by providing an indication that the blockage condition exists in the third fluid flow path in response to determining that the total rate of flow satisfies the fourth flow threshold and does not satisfy the fifth flow threshold. The indication can be provided by providing an indication that the blockage condition exists in the first fluid flow path and the second fluid flow path in response to determining that the total rate of flow satisfies the fifth flow threshold and does not satisfy the sixth flow threshold. The indication can be provided by providing an indication that the blockage condition exists in the second fluid flow path in response to determining that the total rate of flow satisfies the sixth flow threshold and does not satisfy the seventh flow threshold. The indication can be provided by providing an indication that the blockage condition exists in the first fluid flow path in response to determining that the total rate of flow satisfies the eighth flow threshold and does not satisfy the ninth flow threshold. The indication can be provided by providing an indication that a normal operation condition exists in response to determining that the total rate of flow satisfies the ninth flow threshold. The ninth through first flow thresholds respectively correspond to descending levels of flow. The method is performed by a controller of the negative pressure wound therapy apparatus.

The method of any of the preceding paragraphs may also include any combination of the following features described in this paragraph, among others described herein. The first flow threshold corresponds to an expected first rate of flow in the first fluid flow path. The third flow threshold corresponds to an expected first rate of flow in the second fluid flow path. The fourth flow threshold corresponds to an aggregation of the expected first rate of flow in the first fluid flow path and the expected second rate of flow in the second fluid flow path. The fifth flow threshold corresponds to an expected first rate of flow in the third fluid flow path. The sixth flow threshold corresponds to an aggregation of the expected first rate of flow in the first fluid flow path and the expected third rate of flow in the third fluid flow path. The eighth flow threshold corresponds to an aggregation of the expected second rate of flow in the second fluid flow path and the expected third rate of flow in the third fluid flow path. The ninth flow threshold corresponds to an aggregation of the expected first rate of flow in the first fluid flow path, the expected second rate of flow in the second fluid flow path, and the expected third rate of flow in the third fluid flow path.

The method of any of the preceding paragraphs may also include any combination of the following features described in this paragraph, among others described herein. The expected first rate of flow corresponds to the rate of flow in the first fluid path under the normal operation condition. The expected second rate of flow corresponds to the rate of flow in the second fluid path under the normal operation condition. The expected third rate of flow corresponds to the rate of flow in the third fluid path under the normal operation condition.

The method of any of the preceding paragraphs may also include any combination of the following features described in this paragraph, among others described herein. Determining the total rate of flow includes measuring a speed of a motor operating the negative pressure source. Measuring the speed includes measuring a first plurality of motor speeds during a first period of time and averaging the first plurality of motor speeds, the average being indicative of the rate of flow. The method may also include generating one or more graphical user interfaces (GUIs) as described herein.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIGS. 5A-5B illustrate diagrams of a system for applying negative pressure according to some embodiments.

DETAILED DESCRIPTION OF SOME EMBODIMENTS

Overview

Embodiments disclosed herein relate to systems and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
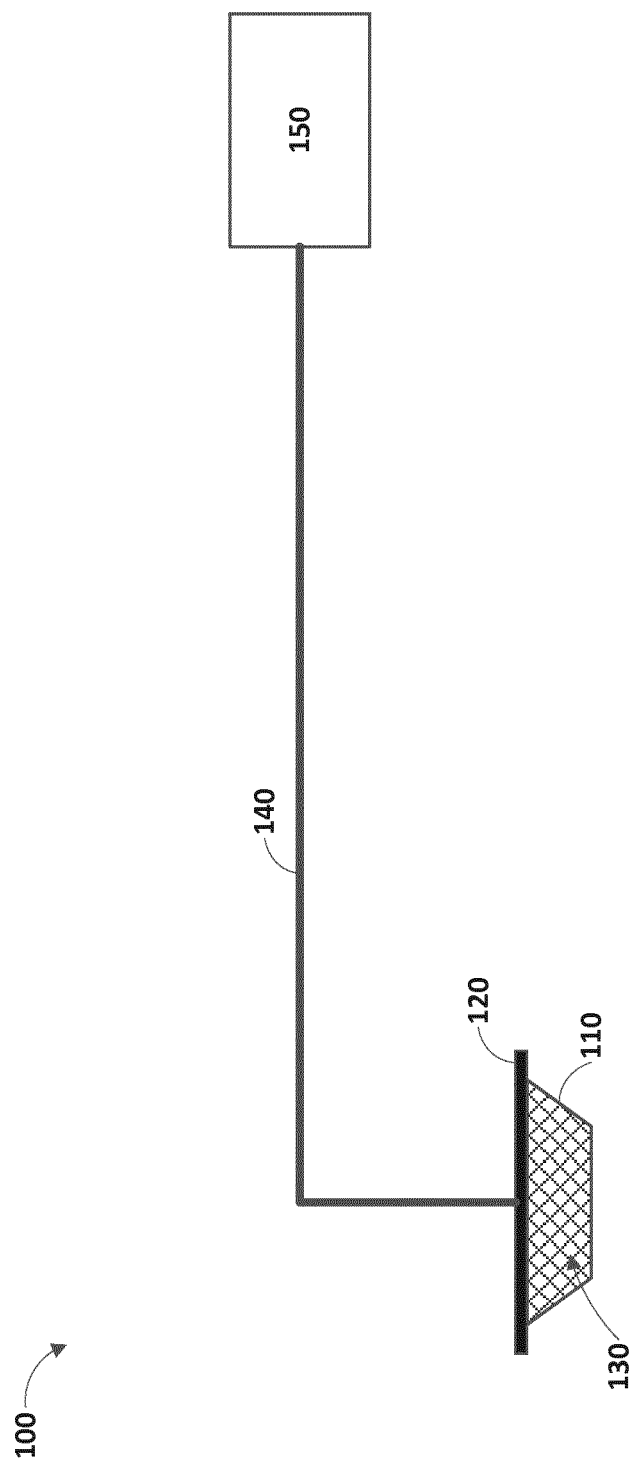
FIG. 1 illustrates a reduced pressure wound therapy system according to some embodiments.

FIG. 1 illustrates an embodiment of a negative or reduced pressure wound treatment (or TNP) system 100 including a wound filler 130 placed inside a wound cavity 110, the wound cavity sealed by a wound cover 120. The wound filler 130 in combination with the wound cover 120 can be referred to as wound dressing. A flow path 140, such as a single or multi lumen tube or conduit, is connected to the wound cover 120 with a negative pressure wound therapy device, for example pump assembly 150, configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure of approximately −80 mmHg, or between about −20 mmHg and −200 mmHg Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg Intermittent therapy can be delivered between low and high negative pressure setpoints. Low setpoint can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg High setpoint can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg During intermittent therapy, negative pressure at low setpoint can be delivered for a first time duration, and upon expiration of the first time duration, negative pressure at high setpoint can be delivered for a second time duration. Upon expiration of the second time duration, negative pressure at low setpoint can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high setpoints and vice versa can be performed according to a step waveform, square waveform, sinusoidal waveform, and the like.

In some embodiments, the TNP system 100 can include multiple wound dressings connected to the pump assembly 150. The performance and wound healing capabilities (such as, fluid management) of the TNP system with multiple wound dressings with the pump assembly 150 can be equivalent to or exceed that of a standard single wound dressing with single pump set-up.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Any of the dressings described herein can be used with Smith and Nephew's Renasys Soft Port connector or interface between the dressing and the pump assembly. For example, Renasys Soft Port connector can be positioned in the flow path 140 and serve as a port for the wound dressing. In other embodiments, other suitable wound dressings can be utilized.

Pump Assembly and Canister

Figure 2:
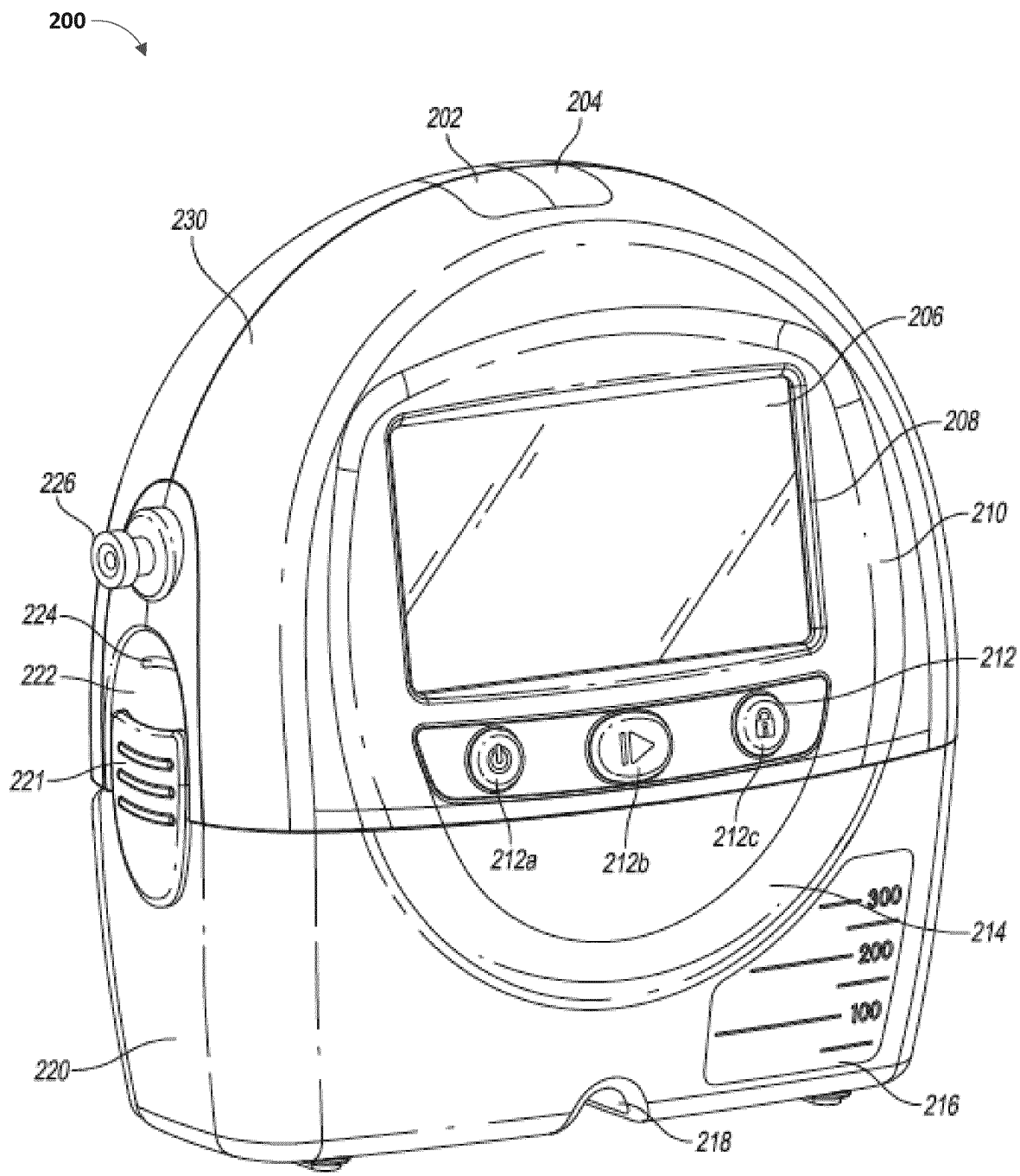
FIG. 2 illustrates a pump assembly and canister according to some embodiments.

FIG. 2 illustrates a front view 200 of a pump assembly 230 and canister 220 according to some embodiments. As is illustrated, the pump assembly 230 and the canister are connected, thereby forming a TNP device or system. The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, no flow condition, canister full condition, or any other similar or suitable conditions or combinations thereof. The pump assembly 230 can include additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained herein, the display 206 can be configured to render a number of screens or graphical user interfaces (GUIs) for configuring, controlling, and monitoring the operation of the TNP system. The pump assembly 230 includes a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons 212 configured to allow the user to operate and monitor the operation of the TNP system. As is illustrated, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 includes an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various features are omitted or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 includes two latches 221 on the sides of the canister. The exterior of the canister 220 can formed from frosted plastic so that the canister is substantially opaque and the contents of the canister and substantially hidden from plain view. The canister 220 includes a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 includes a tubing channel 218 for connecting to the conduit 140. In some embodiments, one or more of these features, such as the gripping portion 214, are omitted or various additional features are added to the canister 220. Any of the disclosed canisters may include or may omit a solidifier.

Electronics and Software

Figure 3:
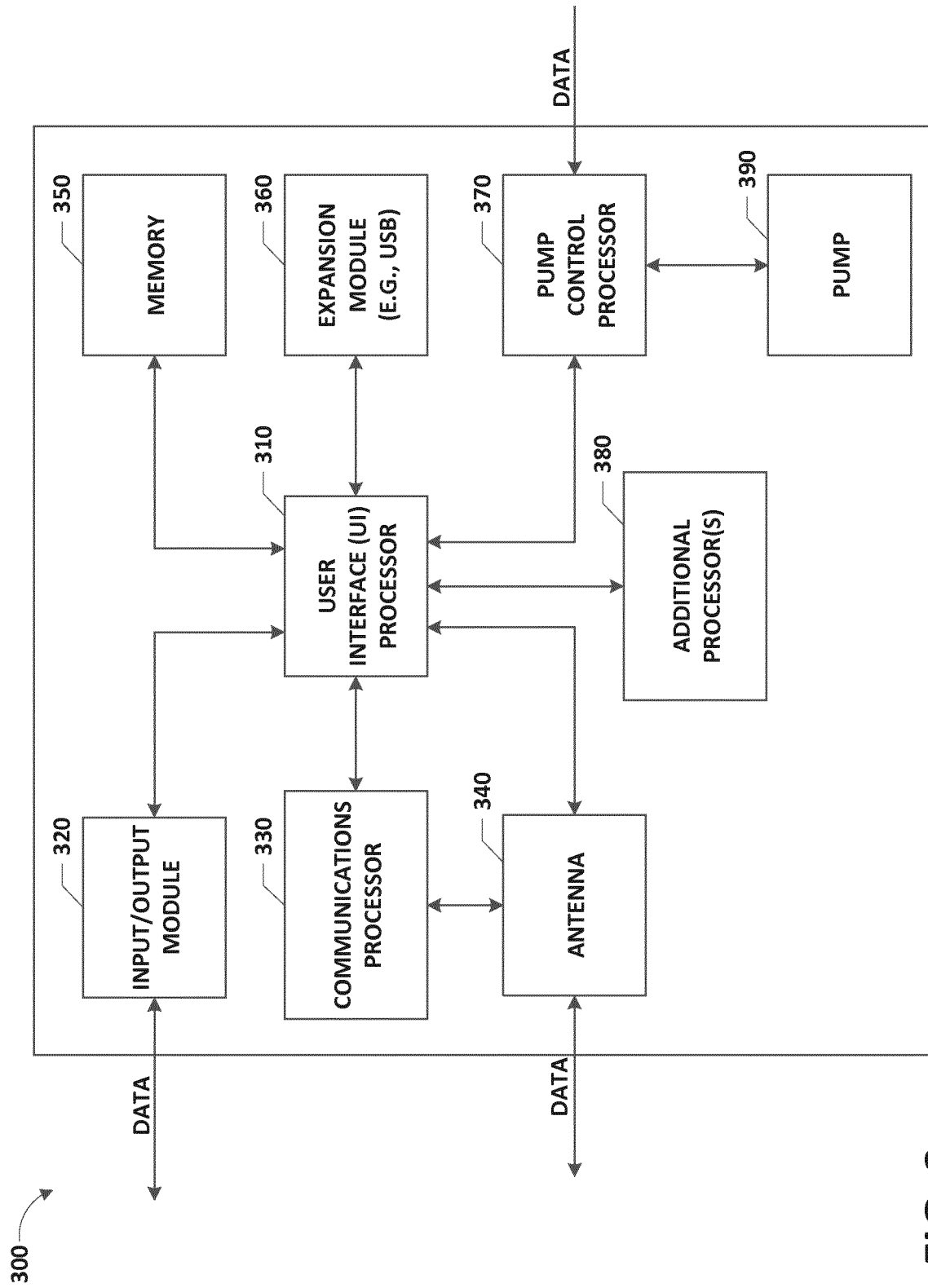
FIG. 3 illustrates an electrical component schematic of a pump assembly according to some embodiments.

FIG. 3 illustrates an electrical component schematic 300 of a pump assembly, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors. It may be advantageous to utilize multiple processors in order to allocate or assign various tasks to different processors. A first processor can be responsible for user activity and a second processor can be responsible for controlling the pump. This way, the activity of controlling the pump, which may necessitate a higher level of responsiveness (corresponding to higher risk level), can be offloaded to a dedicated processor and, thereby, will not be interrupted by user interface tasks, which may take longer to complete because of interactions with the user.

The pump assembly can include a user interface processor or controller 310 configured to operate one or more components for accepting user input and providing output to the user, such as the display 206, buttons 212, etc. Input to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal or external to the processor 310. Any suitable type of memory can be used, including volatile or non-volatile memory, such as RAM, ROM, magnetic memory, solid-state memory, Magnetoresistive random-access memory (MRAM), and the like.

In some embodiments, the processor 310 can be a general purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The pump control processor 370 can be configured to control the operation of a negative pressure source or pump 390. The pump 390 can be a suitable pump, such as a diaphragm pump, peristaltic pump, rotary pump, rotary vane pump, scroll pump, screw pump, liquid ring pump, pump (for example, diaphragm pump) operated by a piezoelectric transducer, voice coil pump, and the like. The pump control processor 370 can measure pressure in a fluid flow path, using data received from one or more pressure sensors, calculate the rate of fluid flow, and control the pump. The pump control processor 370 can control an actuator, such as a pump motor, so that a desired level of negative pressure is achieved in the wound cavity 110. The desired level of negative pressure can be pressure set or selected by the user. In various embodiments, the pump control processor 370 controls the pump actuator (e.g., pump motor) using pulse-width modulation (PWM). A control signal for driving the pump actuator can be a 0-100% duty cycle PWM signal. The pump control processor 370 can perform flow rate calculations and detect various conditions in a flow path. The pump control processor 370 can communicate information to the processor 310. The pump control processor 370 can include internal memory or can utilize memory 350. The pump control processor 370 can be a low-power processor.

A communications processor 330 can be configured to provide wired or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), Wi-Fi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications processor 330 can provide dual GPS/cellular functionality. Cellular functionality can, for example, be 3G functionality.

In such cases, if the GPS module is not able to establish satellite connection due to various factors including atmospheric conditions, building or terrain interference, satellite geometry, and so on, the device location can be determined using the 3G network connection, such as by using cell identification, triangulation, forward link timing, and the like. The pump assembly can include a SIM card, and SIM-based positional information can be obtained.

The communications processor 330 can communicate information to the processor 310. The communications processor 330 can include internal memory or can utilize memory 350. The communications processor 330 can be a low-power processor.

In some embodiments, the pump assembly can track and store various data, such as one or more of positioning data, therapy parameters, logs, device data, and so on. The pump assembly can track and log therapy and other operational data. Data can be stored, for example, in the memory 350.

In some embodiments, using the connectivity provided by the communications processor 330, the device can upload any of the data stored, maintained, or tracked by the pump assembly. For example, the following information can be uploaded to a remote computer or server: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The device can also download various operational data, such as therapy selection and parameters, firmware and software patches and upgrades, and the like. The pump assembly can provide Internet browsing functionality using one or more browser programs, mail programs, application software (e.g., apps), etc.

In some embodiments, the communications processor 330 can use the antenna 340 to communicate a location of the pump assembly, such as a location of a housing of the pump assembly, to other devices in the proximity (for example, within 10, 20, or 50 meters and the like) of the pump assembly. The communications processor 330 can perform one-way or two-way communication with the other devices depending on the implementation. The communications transmitted by the communications processor 330 can include identifying information to uniquely identify the pump assembly relative to one or more other pump assemblies also in the proximity of the pump assembly. For example, identifying information can include a serial number or a value derived from the serial number. The signal strength of the transmitted communications by the communications processor 330 can be controlled (for example, maintained at a constant or substantially constant level) to enable another device to determine a distance to the pump assembly, such as a distance between the device and the pump assembly.

In some embodiments, the communications processor 330 can communicate with other devices in the proximity of the pump assembly so that the communications processor 330 can itself determine a distance from the pump assembly to the other devices. The communications processor 330, in such embodiments, can track and store the distance from the pump assembly to the other devices or indications of change in the distance over time, and the communications processor 330 can later provide this information to the other devices. For instance, the communications processor 330 can determine a duration of time during which the pump assembly has been removed from a coverage area of a device and subsequently report this time to the device upon being returned to the coverage area.

Multiple Dressing Negative Wound Therapy

Figure 4A:
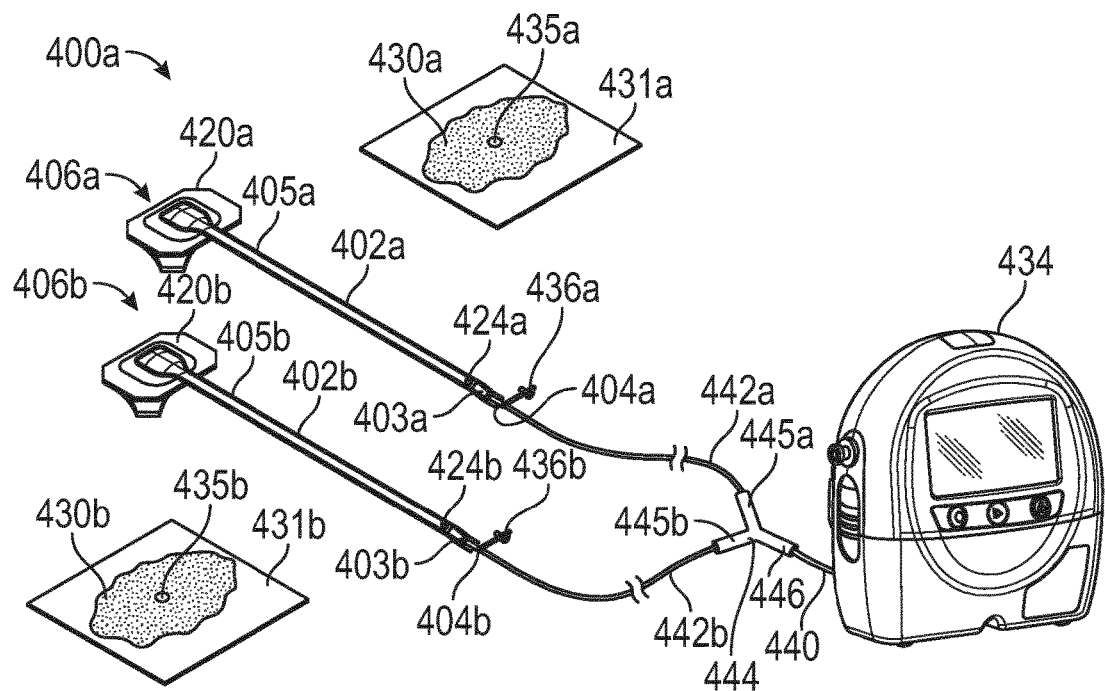
FIG. 4A illustrates a negative pressure wound treatment system including a negative pressure device and illustrating a flexible suction adapter being applied to a wound according to some embodiments.
Figure 4B:
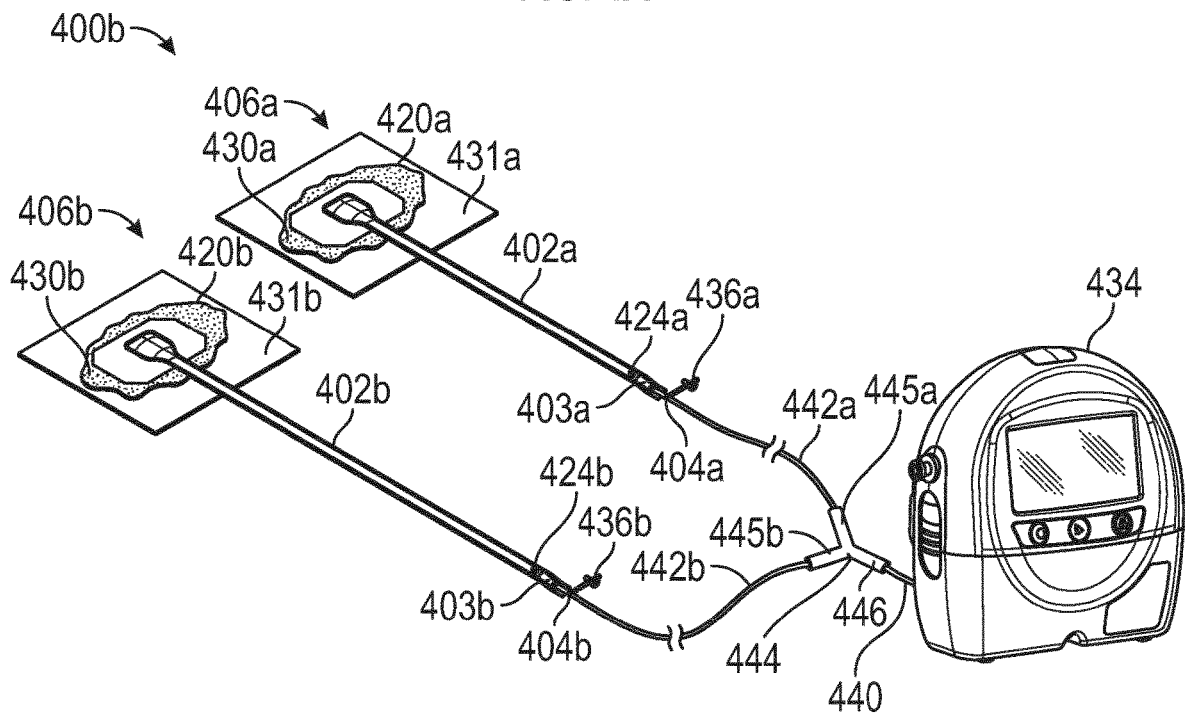
FIG. 4B illustrates an embodiment of FIG. 4A, with the flexible suction adaptor having been placed over a wound.

FIGS. 4A-4B illustrate a negative pressure wound treatment system 400 according to some embodiments. The system 400a, 400b (collectively 400) may include a pump assembly or negative pressure unit 434 capable of supplying negative pressure. In some embodiments, the negative pressure unit 434 is the same as that depicted in FIG. 2. The negative pressure unit 434 may be in fluidic connection with one or more wound dressings 406a, 406b (collectively referred to as 406) so as to supply negative pressure to one or more wounds. In some embodiments, the fluidic connection between a wound dressing 406 and a negative pressure unit 434 is referred to as a fluid flow path (e.g., the path through which fluid aspirated from a wound via negative pressure flows). For instance, a first fluid flow path can include components providing fluidic connection from the negative pressure unit 434 to a first wound dressing 406a. As a non-limiting example, the first fluid flow path can include the path from the wound dressing 406a to the negative pressure unit 434 or the path from the first wound dressing 406a to an inlet of a branching attachment 444 in fluidic connection with the negative pressure unit 434. As illustrated, the system 400 can include a plurality of wound dressings (and corresponding fluid flow paths) in fluidic connection with the negative pressure unit 434 via a plurality of Smith & Nephew's Renasys Soft Port connectors. Each wound dressing and fluid flow path can include a variety of features or elements which match or are similar to features or elements of another wound dressing or fluid flow path within the system. For ease of reference, one or more corresponding features or elements (for example, bridge 402a and bridge 402b of Renasys Soft Port connectors) may be collectively referred using a reference number without a corresponding letter. For example, bridge 402a and bridge 402b may be collectively referred to as bridge 402. However, it should be noted that, in some embodiments, elements which have been collectively referred to are not identical and can have different features or attributes.

Referring to FIG. 4A, the system 400a may include a Renasys Soft Port connector including a bridge 402 having a proximal end 403 and a distal end 405 and an applicator 420 at the distal end 405 of the bridge 402 forming a flexible suction interface or adapter. A connector 404 can be disposed at the proximal end 403 of the bridge 402, so as to provide fluidic connection between the wound dressing 406 (shown in FIG. 4B) and the negative pressure unit 434. A cap 436 may be provided with the system 400 (and can in some cases, as illustrated, be attached to the connector 404). The cap 436 can be useful in preventing fluids from leaking out of the proximal end 403 when the connector is disconnected from the negative pressure unit 434. The negative pressure unit 434 can include a canister or other container for the storage of wound exudates and other fluids that may be removed from the wound. Alternatively or in addition, the wound dressing 406 may collect the wound exudates and other fluids, and the canister may not be present. In some embodiments, multiple canisters are provided, for instance, one canister per wound dressing. In some embodiments, the negative pressure unit 434 can be a Renasys Touch device, as manufactured by Smith & Nephew. In some embodiments, connectors other than Renasys Soft Port or devices other than Renasys Touch can be used.

The bridge 402 can include upper and lower channel layers (not shown) for channeling wound exudate away from the wound and for transmitting negative pressure or vented air to the wound site. The upper and lower channel layers can be elongate layers extending from the proximal end 403 to the distal end 405 and may each include a porous material, including for example open-celled foams such as polyethylene or polyurethane. One or more of the upper and lower channel layers may include a fabric, for example a knitted or woven spacer fabric or a nonwoven material. Suitable materials may also include terry-woven or loop-pile materials. The fibers may not necessarily be woven, and can include felted and flocked fibrous materials. In some embodiments, the upper channel layer is optional, and the system may instead be provided with an open upper channel.

FIG. 4B illustrates an embodiment of FIG. 4A, with the flexible suction adaptor having been placed over a wound. In some embodiments, the applicator 420 is placed over an aperture 435 formed in a drape 431 that is placed over a suitably-prepared wound 430, which may in some cases be filled with a wound packing material such as foam or gauze. Subsequently, with the negative pressure unit 434 connected via a tube 440 or an inlet manifold branching attachment or connector 444 to the connector 404, the negative pressure unit 434 is activated, thereby supplying negative pressure via the fluid flow paths to the wounds. Application of negative pressure may be applied until a desired level of healing of the wounds 430 is achieved. Although two wounds and wound dressing are illustrated in FIGS. 4A-4B, the negative pressure unit 434 can provide treatment to more than two wounds in some embodiments. In some implementations, negative pressure wound therapy can be provided to a single wound.

Attachment

Figure 6:
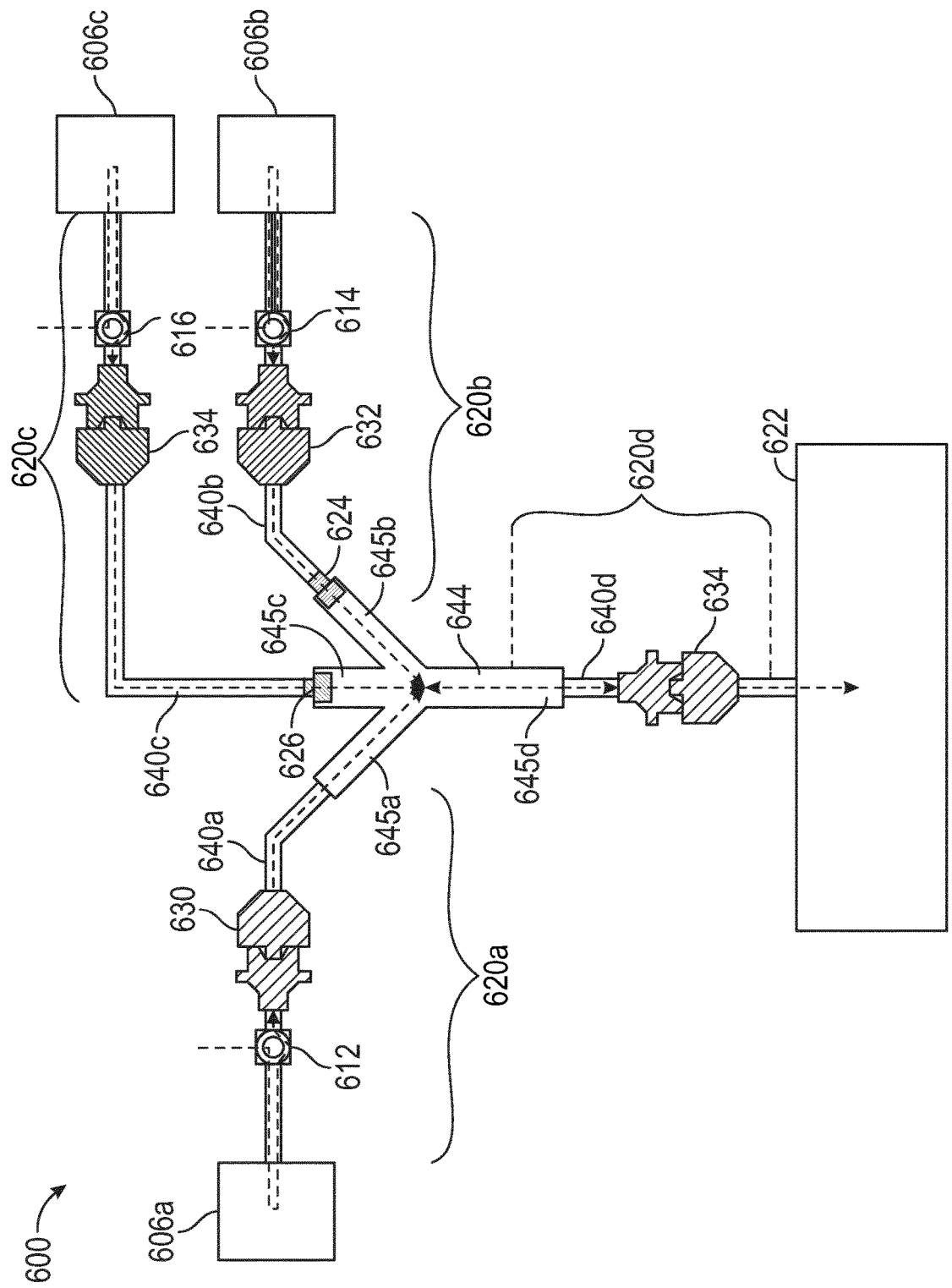
FIG. 6 illustrates a diagram of a system for applying negative pressure according to some embodiments.

The negative pressure unit 434 may be in fluidic connection with the wound dressings 406 via one or more tubes 440, 442, one or more bridges 402, or via an inlet manifold branching attachment 444. For example, the negative pressure unit 434 may be in fluidic connection with a plurality of wound dressings 406 via a tube 440, an inlet manifold branching attachment 444, a tube 442, and a bridge 402. As another example, the manifold branching attachment 444 can be connected directly to the negative pressure unit 434 without using the tube 440. As illustrated in FIGS. 4A-4B, the inlet manifold branching attachment 444 can be configured to connect the negative pressure unit 434 to a plurality of fluid flow paths via a plurality of dressing conduit attachment portions 445a, 445b. The inlet manifold branching attachment 444 can include any number of dressing conduit attachment portions 445 configured to be fluidically connected to a negative pressure attachment portion 446 via a joint. For example, the inlet manifold branching attachment can include two dressing conduit attachment portions 445a, 445b, three dressing conduit attachment portions 645a, 645b, 645c (as shown in FIG. 6), or more than three dressing conduit attachment portions.

The plurality of dressing conduit attachment portions 445 can include a first dressing conduit attachment portion 445a and a second dressing attachment portion 445b. However, it will be understood that more or fewer dressing conduit attachment portions can be included in the inlet manifold branching attachment 444. Each of the dressing conduit attachment portions 445 includes a shaft extending away from a joint and including an inlet distal the joint. The inlets are configured to fluidically connect at least a portion of a fluid flow path to the negative pressure unit 434.

The inlet manifold branching attachment 444 can also include one or more negative pressure attachment portions 446. Each of the negative pressure attachment portions 446 can include a shaft extending away from the joint and an inlet distal the joint. The inlet(s) can be configured to fluidically connect to the negative pressure unit 434. For instance, the inlets can include male or female non-luer connectors to attach to a corresponding male or female connector of a conduit or pump. In some embodiments, a negative pressure attachment portion 446 is attached to the negative pressure unit 434 via a tubing 440 or other conduit. A negative pressure attachment portion 446 can also be attached directly (or can be integrated with) a housing of the negative pressure unit 434.

The inlet manifold branching attachment 444 or the conduit can include incorporated one or more valves, clamps, caps, air leaks, or other flow regulator mechanisms which may be configured to admit fluid into a fluid flow path or, alternatively, block or restrict flow or passage of fluid through a fluid flow path. In some embodiments, valves, air leaks, or other flow regulation mechanisms in the inlet manifold branching attachment 444 can be opened or closed electronically. For instance, a controller of the negative pressure unit 434 can communicate with the valves, air leaks, etc. to open or close each one individually or as a unit. This communication can be wired or wireless.

The dressing conduit attachment portions 445 can include shafts forming the top portions of a Y—(two wound), W—(three wound) or other shape of the inlet manifold branching attachment. The proximal ends of dressing conduit shafts and the distal end of the pump conduit shaft can meet at a joint. In some embodiments, the joint can include a hinge that allows rotation of the shafts about the joint. In some embodiments, the inlet manifold branching attachment can be a W-shaped connector (as illustrated in FIG. 6). In embodiments such as these, the inlet manifold branching attachment can include three or more dressing conduit attachment portions and one negative pressure attachment portion.

The inlet manifold branching attachment can include rigid plastic or flexible plastic tubing and can also or alternatively be encased in a soft silicone sleeve to increase patient comfort and prevent the inlet manifold branching attachment 444 from becoming a pressure point.

In some embodiments, utilizing the inlet manifold branching attachment to attach a negative pressure unit to a plurality of wound dressings 406, the negative pressure unit can aspirate fluid from multiple wounds 430 simultaneously. The performance and wound healing capabilities (such as, fluid management) of such system can be equivalent to or exceed that of a standard single wound dressing with single pump set-up.

In some embodiments, an integrated inlet manifold (not shown) can be used in place of an inlet manifold branching attachment 444. In examples such as these, inlet manifolds can be incorporated (e.g., directly attached) into the negative pressure unit 434 or pump housing such that the one or more fluid flow paths can fluidically connect to the pump via one or more inlets of the integrated inlet manifolds. The integrated inlet manifolds can include a splitting attachment (similar to the Y-shaped or W-shaped branching attachment described herein) or can include one or more separately integrated inlets in fluidic connection with the pump.

Controlled Air/Fluid Leaks

In certain embodiments, an air leak 424 (sometimes referred to as a fluid leak or a controlled air leak) may be disposed in a fluid flow path, such as, at the proximal end 403 of the bridge portion 402. The air leak 424 may include an opening or channel extending through an upper layer of the bridge 402, such that the air leak 424 is in fluidic communication with an upper channel (not shown) of the bridge 402. In some embodiments, upon the application of suction to the system 400, air, gas, or other fluid will enter through the air leak 424 and flow in the fluid flow path. In some cases, the air will move from the proximal end 403 to the distal end 405 along the upper channel. The air or fluid can then be suctioned into a lower channel (not shown) by passing through apertures through the distal ends of one or more layers of the bridge 402.

In some embodiments, the air leak 424 can be located at the proximal end 403 of the bridge portion 402 so as to minimize the likelihood of wound exudate or other fluids coming into contact and possibly occluding or interfering with the air leak 424 or an optional filter (such as one or more of odor, anti-bacterial, or anti-microbial filter) included with the air leak 424. However, it should be understood that one or more air leaks can be located anywhere in the system or within a fluid flow path including but not limited to the wound dressing 406, the bridge 402, a tube 442, 440, and the manifold branching attachment 444.

A filter (not shown) can be placed in the air leak 424 to prevent outside contaminants, such as microorganisms, dust, or other foreign matter from entering the wound area. In some embodiments, the filter is a microporous membrane capable of excluding microorganisms and bacteria, and which may be able to filter out particles larger than 45 μm. In some embodiments, the filter 425 can exclude particles larger than 1.0 μm or particles larger than 0.2 μm. Advantageously, some embodiments may provide for a filter that is at least partially chemically-resistant, for example to water, common household liquids such as shampoos, and other surfactants. Accordingly, in some embodiments, the filter may be designed so that a patient may use the system 400 in a shower or other similar environment without occluding the air leak 424. In some embodiments, reapplication of vacuum to the system 400 or wiping of the exposed outer portion of the filter may be sufficient to clear any foreign substance occluding the filter. The filter may be composed of a suitably-resistant polymer such as acrylic, polyethersulfone, or polytetrafluoroethylene, and may be oleophobic or hydrophobic. In some embodiments, the filter may include a supporting backing layer, for example a nonwoven polyester support.

The filter provided in the air leak 424 in certain embodiments may be useful in a system 400 for use with more ambulatory and active patients. For example, a chemically-resistant filter may permit a patient to bathe or shower without damaging the filter's functionality when reconnected to a source of negative pressure. Any occlusion or fluid blocking the air leak 424 could then be cleared by, for example, wiping off the filter or re-applying negative pressure to the system 400. Such a system could have the advantage that the system 400 and any assorted wound dressing materials, if present, would not need to be removed and then re-applied should a patient need to be disconnected from the source of negative pressure, for example incidental to bathing. This could entail significant advantages in improving the cost-effectiveness and ease of use of the present treatment system.

In some embodiments, alternative or additional mechanism for admitting air, gas, or other fluid into the system can be used. For example, one or more valves can be placed in the fluid flow path. As described herein, the one or more valves can be controlled by the controller.

Determining Operating Conditions

In some embodiments, the system 400 can apply negative pressure to one or more wounds. The level of negative pressure at one or more of the wounds (for example, under one or more wound dressings) can be sufficiently close to the negative pressure level at the source of negative pressure. For example, an acceptable level of pressure maintained at the wound may be within ±1 mmHg, ±5 mmHg, ±10 mmHg, ±25 mmHg, and the like of the negative pressure setpoint. In some embodiments, this pressure can be maintained at this level within 95% (or another suitable percentage) of the time that the system 400 has negative pressure applied to it. In some embodiments, acceptable pressure levels may include pressure ranges between −40 to −120 mmHg. However, other pressure levels may be used as described herein.

As described in more detail herein, the system 400 can utilize one or more air leaks in one or more of the fluid flow paths to determine one or more operating conditions within the system 400. For example, an air leak can be a controlled air leak that can admit a relatively constant air, gas, or other fluid flow into a fluid flow path. In some embodiments, the flow into the fluid flow path from an air leak does not appreciably increase as additional negative pressure is applied to the system 400. However, the presence of an air leak in the system 400 may maintain substantially constant baseline flow through the system when steady state has been achieved (for example, when the negative pressure set point has been reached). In turn, presence of the air leak may require the negative pressure source to work harder to maintain the desired level of negative pressure at the wound(s). Accordingly, the system may determine the presence of one or more operating conditions (such as a blockage, leakage, canister full, and the like) by monitoring the flow through the fluid flow path(s), which can be measured directly or indirectly based on, for example, monitoring an activity of the negative pressure source.

In some embodiments, each fluid flow path may include an air leak (such as illustrated in FIGS. 4A-4B) and each air leak of a respective fluid flow path can admit a different flow rate of air, gas, or other fluid into the system. In other words, each air leak of the system can have a different leak rate. For example, the leak rate of an air leak can be based at least in part on the size or shape of the air leak, whether the air leak includes a filter, the size or porous level or a filter, a level of occlusion of the air leak or the filter, and the like. The fluid admitted into a fluid flow path increases the flow rate of that fluid flow path.

Accordingly, each fluid flow path of the system 400 can have a different flow rate. The total flow rate (TFR) of the system 400 (e.g., the aggregation of the flow to each of the wound dressings) can be monitored, calculated, or determined and then used to determine an operating condition of the system 400. Operating conditions can, for instance, include a "no flow" condition (e.g., all of the flow paths are blocked), a blockage condition of one or more flow paths (e.g., a blockage condition exists in a first fluid flow path, a blockage condition exists a second fluid flow path, etc.), a canister full condition, normal operation (e.g., no blockages are present in any of the fluid flow paths), and the like.

In some embodiments, the system 400 is capable of providing an indication, such as alarm, to tell the patient or a caregiver an operating status of the system 400 based on a comparison of the determined total flow rate and one or more flow thresholds. In some embodiments, the flow thresholds corresponding to operating conditions of the system 400 are pre-determined. In some embodiments, the flow thresholds are based at least in part on dynamic measurements or calculations of the system 400, such as a flow rate or pressure, during a particular mode of the system (e.g., a calibration mode).

Figure 5B:
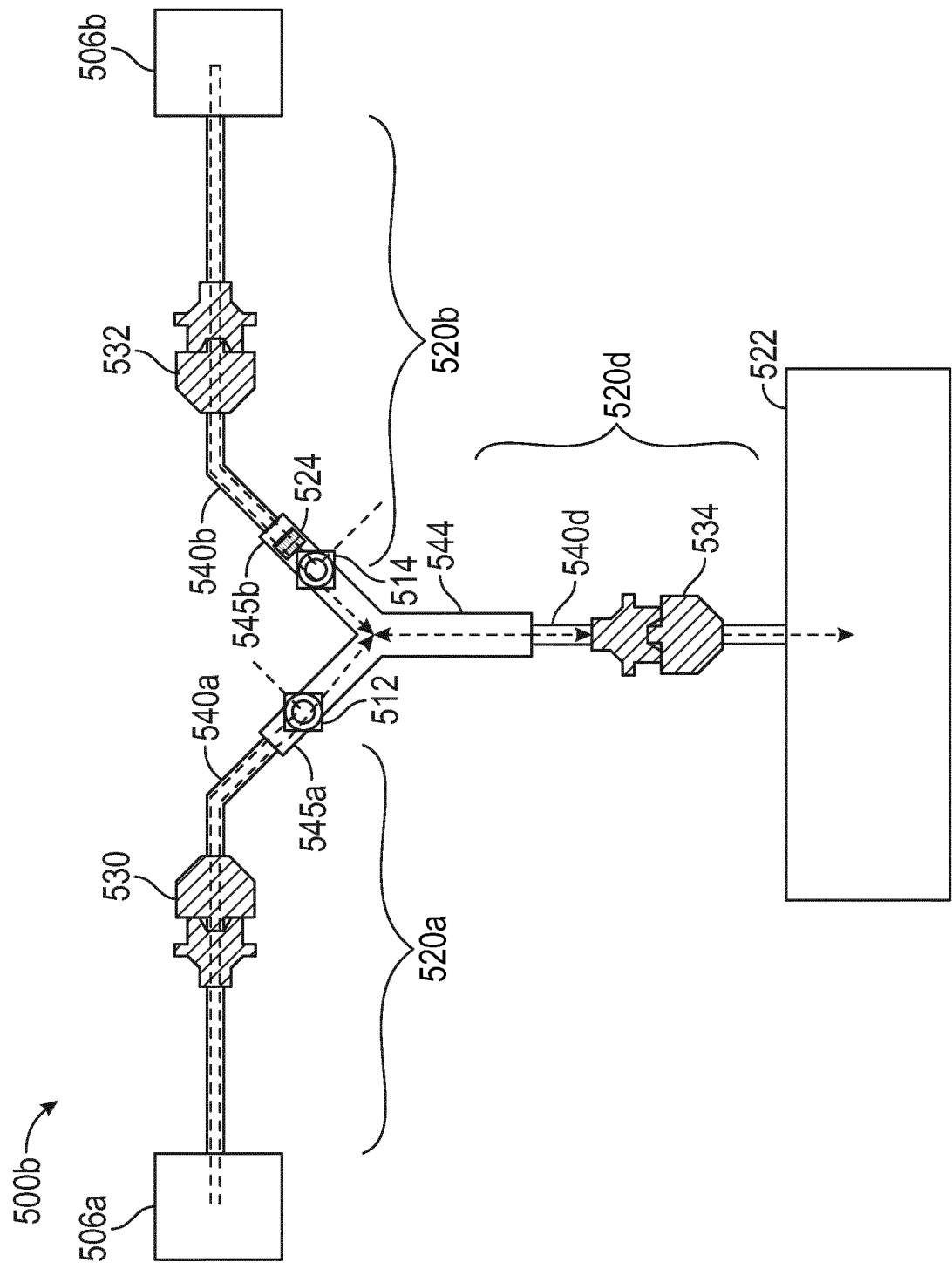

FIGS. 5A-5B illustrate diagrams of a system for applying negative pressure according to some embodiments. As illustrated, the system 500a, 500b (collectively 500) includes a source of negative pressure 522 in fluidic connection with wound dressings 506a, 506b via fluid flow path 540d, inlet manifold branching attachment 544, and fluid flow paths 540a, 540b, so as to supply negative pressure to one or more wound sites. Each of first fluid flow path 540a and the second fluid flow path 540b include an air leak 512, 514 configured to admit fluid into the respective fluid flow path.

As illustrated in FIGS. 5A-5B, an air leak 512, 514 may be disposed at any suitable location in a fluid flow path. For instance, an air leak can be incorporated into an inlet manifold branching attachment 544 as illustrated in FIG. 5B or upstream (closer to the wound) as illustrated in FIG. 5A. In some embodiments, one or more of single or dual lumen connectors 530 and 532 can incorporate an air leak. In some embodiments, the air leaks can be electronically or electromechanically adjusted by a controller of the system to close or widen the leak. For instance, a controller can communicate with the air leaks to open or close each air leak individually or as a unit. For instance, the air leaks can be solenoid valves. The communication between the air leaks and the controller can be wired or wireless.

In some embodiments, the system 500 is able to maintain a constant leak rate through an air leak while negative pressure is applied through a source of negative pressure. Some embodiments may support an air leak of 1, 2, 3, 4, 5, 6, 7, 8, 9 mL/min or more (+/−0.5 mL/min or another suitable deviation). Some embodiments may support an air leak of 10, 20, 30, 40, 50, 60, 70, 80, 90 mL/min, or more (+/−a few mL/min or another suitable deviation). Some embodiments may support an air leak of 0.1, 0.2, 0.3, 0.4, 0.5, 0.6, 0.7, 0.8, 0.9 L/min, or more (+/−a few centiliters/min or another suitable deviation). In some instances, the leak rate can be discussed in terms of controlled leak pathways (CLPs), where CLP is a suitable constant. For instance, an air leak may have a leak rate of 0.25, 0.5, 1, 2, 3, 4, 5, 6, 7, 8, 9, 10, or more. For example, assuming that a leak rate of 0.1 L/min, 1 CLP may correspond to 0.1 L/min, 5 CLPs may correspond to 0.5 L/min, and so on. The negative pressure source must work harder in presence of higher intensity air leak, which can drain the power source faster. Thus, in some embodiments, a relatively low leak rate is chosen.

In some embodiments, the first air leak 512 has a different leak rate different than the second air leak 514. For instance, the first air leak can have a leak rate of 1 CLP and the second air leak can have a leak rate of 2 CLP. Alternatively, the first air leak can have a leak rate of 0.5 CLP and the second air leak can have a leak rate of 1 CLP. However, it should be noted that the leak rates of system can be any suitable flow rates. Because of the differing leak rates, the first and second fluid flow paths 520a, 520b can have differing flow rates. Alternatively, the first air leak 512 and the second air leak 514 can be equal or approximately equal (e.g., +/−0.1 L/min or another suitable deviation). For instance, the first air leak 512 and the second air leak 514 can each have a leak rate of 1 CLP. However, it should be noted that the leak rates of system can be any suitable flow rates. Because of the equal leak rates, the first and second fluid flow paths 520a, 520b can have similar flow rates. In some embodiments, the total flow rate (TFR) of the system is an aggregation of the flow coming from the one or more wound dressings of the system. Thus, in some instances, the TFR can be equivalent to the flow rate of fluid flow path 520d.

Flow Rate Monitoring

The system 500 can monitor or determine a TFR in the system based, for example, on monitoring the activity of the negative pressure source 522. In certain embodiments, flow rate monitoring can be performed by a pump control processor (such as the pump control processor 370 of FIG. 3) alone or in combination with a processor (such as the user interface processor 310 of FIG. 3). Monitoring the flow rate can be used, among other things, to ensure that therapy is properly delivered to one or more wounds, to detect blockages, canister full conditions, no flow conditions, or leaks in one or more fluid flow paths, high pressure, ensure that the flow rate is not unsafe (e.g., dangerously high), etc.

In certain implementations, the system performs flow rate monitoring directly by, for example, using one or more flow meters positioned in the fluid flow path. In some embodiments, the system performs flow rate monitoring indirectly by measuring or monitoring activity of the negative pressure source, such as by monitoring the activity of an actuator. For instance, the system can monitor the activity of a vacuum pump motor, including monitoring the speed of the vacuum pump motor using a tachometer, monitoring current or voltage supplied to the pump (such as, the current or voltage of PWM signal), and the like. The system can continuously monitor one or more of these characteristics to determine activity of the negative pressure source.

In some embodiments, a tachometer (such as a Hall effect sensor) can be used to measure the level of activity of pump motor, The tachometer can be read periodically, such as every 100 msec or another suitable time period, and periodic readings made over a time duration, such as 32 sec or another suitable time duration, can be combined (e.g., averaged). Combined tachometer readings can be used for determining the flow rate, which can in turn be used for leak detection, blockage detection, limiting the maximum flow rate, etc. Combined tachometer readings (e.g., in counts or pulses) can be converted to a flow rate (e.g., in mL/min) using one or more conversion equations or tables so that a TFR of the system (e.g., an aggregation of the flow in each fluid flow path associated with a wound dressing) is determined. In some embodiments, the TFR is determined according to the following equation:

$$TFR = C_1 * F * P + C_2$$

where TFR is the total flow rate, F is the frequency of the pump tachometer signal, P is pressure produced by the pump (for example, negative pressure setpoint), and $C_1$ and $C_2$ are suitable constants (determined for given negative pressure source). The determined flow rate can be compared to various flow rate thresholds, such as one or more blockage thresholds, to determine a presence of a particular condition, such as a blockage, leakage, canister full, etc.

In some embodiments, a total flow rate can be determined for the system. TFR can correspond to the sum of the leak rates seen by the negative pressure source. For instance, an expected TFR can be determined, for instance, in a calibration mode, using one or more conversion equations or tables, and the like. The expected TFR can correspond to the TFR of the system in steady state operation (for example, when the negative pressure set point has been reached) if no air leaks are present and the like. The system can then monitor the TFR and compare it to one or more leak or flow rate thresholds to determine a presence of a particular condition, such as a blockage, no flow, normal operation, canister full, etc. In some implementations, the expected TFR can be determined in non-steady state. In certain cases, more than one expected TFR can be utilized.

In some embodiments, a blockage condition is detected when the determined flow rate fails to satisfy one or more flow thresholds. For instance, a blockage alarm can be enabled if the blockage condition is present for a period of time, such as 30 seconds or another suitable period of time. This approach can implement hysteresis so that transient events do not cause the system to erroneously report presence of one or more operating conditions. In embodiments where the system includes more than one wound dressing, a different blockage alarm can be enabled for each wound dressing. The blockage alarm can be disabled when the determined flow rate exceeds the one or more flow thresholds. In some embodiments, the system can differentiate between a blockage in one or more fluid flow paths and canister full conditions.

In some embodiments, blockages and presence of fluid in one or more fluid flow paths are detected by processing data from one or more pressure sensors (not shown), which can be positioned in any suitable location in the flow path. In some embodiments, a pressure sensor is positioned at or near an inlet of the negative pressure source. This detection can be enhanced by changing one or more settings of the pump, such as increasing pressure level delivered by the pump, decreasing the pressure level, stopping the pump, changing the pump speed, changing a cadence of the pump, and the like.

In some embodiments, flow rate can be estimated as the air, gas, or other fluid volume moving in the fluid flow path per unit of time normalized to standard temperature and standard pressure (e.g., 1 atm). Flow rate can be periodically computed, such as every 250 milliseconds or any other suitable time value, according to the following formula:

$$TFR = Slope * Tachometer + Intercept$$

Tachometer is short tachometer average (for example, an average of most recent tachometer readings (e.g., over 2.5 seconds or another suitable period of time), which can be measured in Hz) and Slope and Intercept are constants that are based on the negative pressure setpoint. The values for Slope and Intercept can be determined for possible pressure setpoints (e.g., −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg) for a given negative pressure source. The flow as a function of the pump speed may not be a best fit as a single line because the pump can be designed to be more efficient at lower flow rates. Because of this, slope and intercept values can be pre-computed for various setpoints and various pumps. As described herein, the determined flow rate can be compared to various flow thresholds to determine a presence of a particular operating condition, such as a blockage condition, no flow condition, canister full condition, abnormal condition, normal condition, etc.

In addition, the system can determine and monitor pressure in a fluid flow path using one or more sensors. For instance, a fluid flow path can include a pressure sensor at or near a wound dressing 406, at or near an inlet manifold branching attachment 444, or anywhere else on the fluid flow path. In some embodiments, the pump assembly includes a pressure sensor in or near the inlet (or canister connection) of the pump assembly. This pressure sensor can measure the pressure in the canister (or in or near the dressing in a canisterless system). The pump assembly can continuously measure pressure in the canister, such as every millisecond or any other suitable duration. A suitable number of latest pressure sensor readings can be averaged to mitigate the effects of one or more errant readings.

Based on the determined total flow rate, the pump assembly can monitor and detect various operating conditions as described herein. One or more of these conditions can be detected by, for instance, flow chart 700 or 800 illustrated in FIGS. 7 and 8. A blockage in one or more fluid flow path can be determined by comparing the total flow rate to one or more flow thresholds. The comparison can implement hysteresis, such as be continuously or substantially continuously performed over or during a period of time, such as 2 minutes or any other suitable duration. The one or more flow thresholds can be selected or determined based on the particular pressure setpoint since the expected TFR may also depend on the setpoint. That is, to detect blockages, the pump assembly can utilize a plurality of flow thresholds corresponding to particular pressure setpoints. Alternatively or in addition, flow thresholds can be selected or determined based on the leak rates of the one or more air leaks. As explained herein, the flow rate can be indirectly determined by detecting and monitoring the pump speed.

If one or more flow thresholds are satisfied or not satisfied (e.g., over a period of time), the system determines that there is a blockage in at least one of the fluid flow paths and provides an indication, which can include activating an alarm (e.g., visual, audio, or tactile), pausing operation of the negative pressure, or the like. For example, to determine presence of a blockage, the pump assembly can determine whether the total flow rate satisfies, exceeds, or falls below a flow threshold during a 2 minute period of time or during any other suitable period of time. Because total flow rate may be updated at periodic time intervals due to periodic sampling of the tachometer, the pump assembly may compare the total flow rate as it is being updated to the flow threshold over the 2 minute period of time. Blockage can be detected provided that each total flow rate determined during the 2 minute interval satisfies, exceeds, or falls below a flow threshold. Alternatively or additionally, blockage can be detected if the majority of calculated total flow rates, such as 9 out of 10 or any other suitable number, satisfy, exceed, or fall below a flow threshold. Detected blockages may be cleared when the total flow rate falls below (or exceeds) one or more flow thresholds for a period of time, such as 5 seconds or any other suitable duration.

The threshold value can be any suitable flow threshold, such as a value selected or determined based on the negative pressure setpoint and expected flow rate in the fluid flow path, which can be determined as described herein.

In some embodiments, one or more flow sensors or flow meters can be used to directly measure the fluid flow. In some embodiments, the pump assembly can utilize one or more of the techniques described herein in parallel to control the pump and to detect various conditions. The pump assembly can be configured to suitably arbitrate between using parameters determined by different techniques. For example, the pump assembly can arbitrate between flow rates determined indirectly, such as based on the pump speed as measured by a tachometer, and directly, such as by using a flow meter. In certain embodiments, the pump assembly can indirectly determine the flow rate and resort to direct determination of the flow rate when needed, such as when indirectly determined flow rate is perceived to be inaccurate or unreliable.

In some embodiments, selecting or activating a Y- or W-connect features for treatment of multiple wounds, can alter or modify detection of one or more operating conditions, such as blockages, leaks, canister full condition, and the like. Activating the Y- or W-connect features can adjust one or more of various thresholds described herein. In some embodiments, the system automatically detects that Y- or W-connector is present. For instance, if a single wound dressing is connected having a leak rate of 1 CLP, the system can automatically detect that a Y-connector is present by detecting a leak higher than the expected 1 CLP leak. For instance, the system may prompt the user to confirm that another flow path with, for example, with a leak rate of 2 CLP is present. Once the user confirms, the system will know to detect blockage and can determine flow thresholds based at least in part of the determination of the leak rates. A similar determination can be used for W-connector with three flow paths. For instance, continuing with the previous example, if the system detects a leak higher than the expected 3 CLP leak, the system can detect that a W-connector is present and may prompt the user to confirm that another flow path with, for example, a leak rate of 4 CLP is present. In some embodiments, similar approaches can be utilized when more than 3 wounds are being treated.

FIG. 6 illustrates a diagram of a system 600 for applying negative pressure according to some embodiments. As illustrated, the system 600 includes a source of negative pressure 622 in fluidic connection with wound dressings 606a, 606b, 606c via fluid flow path 640d, inlet manifold branching attachment 644, and fluid flow paths 640a, 640b, 640c so as to supply negative pressure to one or more wound sites. Each of first fluid flow path 640a, the second fluid flow path 640b, and the third fluid flow path 640c include air leaks 612, 614, 616, respectively, configured to admit fluid into the respective fluid flow path. As described herein, the first air leak 612 (corresponding to the first fluid flow path 640a) can have a leak rate different from a leak rate of the second air leak 614 (corresponding to the second fluid flow path 640b) and the third air leak 616 (corresponding to the third fluid flow path 640c). The second and third air leaks can also have different leak rates. For example, air leak 612 can be 1 CLP, air leak 616 can be 3 CLP, and air leak 614 can be 5 CLP. Accordingly, the total flow rate (e.g., the flow rate of fluid flow path 640d) of the system 600 can be monitored (e.g., measured or calculated) and used to determine an operating condition of the system 600. As explained herein, in some embodiments, one or more air leaks 612, 614, and 616 can be positioned in any suitable location in the fluid flow path.

The system can also include one or more of a plurality of single or dual lumen connectors 630, 632, 634 disposed within each of the fluid flow paths 620a, 620b, 620c, 620d. In various examples, the system can include one or more identifiers configured to indicate to a user which fluid flow path, wound dressing, outlet of the inlet branching attachment 644, and lumen connector correspond to each other (e.g., are within the same fluid flow path). For example, each of the wound dressings, outlets of the inlet branching attachments, and lumens can include at least one of a printed glyph, a printed icon, an embossed glyph, an embossed icon, a braille character, or a color-coding. The identifiers of corresponding components can match so as to indicate to a user what is connected. For example, the outlet 624 of the inlet manifold branching attached 644, the connector 632 and the wound dressing 606b can each include a pink color-coding to designate they are each associated with the second fluid flow path 620b. Similarly, the outlet 626 of the inlet manifold branching attached 644, the connector 634 and the wound dressing 606c can each include a green color-coding to designate they are each associated with the third fluid flow path 620c. In some embodiments, the system could correlate colors to detected blockages to assist the user. For example, if a blockage is detected on the second fluid flow path, the display can present a colored icon on the display. In this example, the system may present a pink colored icon. In some embodiments, these approaches for identification and indication can be used in a system treating two wounds (such as the system illustrated in FIG. 5) or a system treating more than three wounds.

As described with respect to FIG. 4, the inlet manifold branching attachment 644 can be a W-shaped connector including three dressing conduit attachment portions 645a, 645b, 645c and one negative pressure attachment portion 645d. Utilizing the inlet manifold branching attachment 644 to attach the negative pressure source 622 to the wound dressings 606, the negative pressure source 622 can draw pressure in the multiple wound dressings 606 simultaneously. The performance and wound healing capabilities (such as, fluid management) of such system can be equivalent to or exceed that of a standard single wound dressing with single pump set-up.

Figure 7:
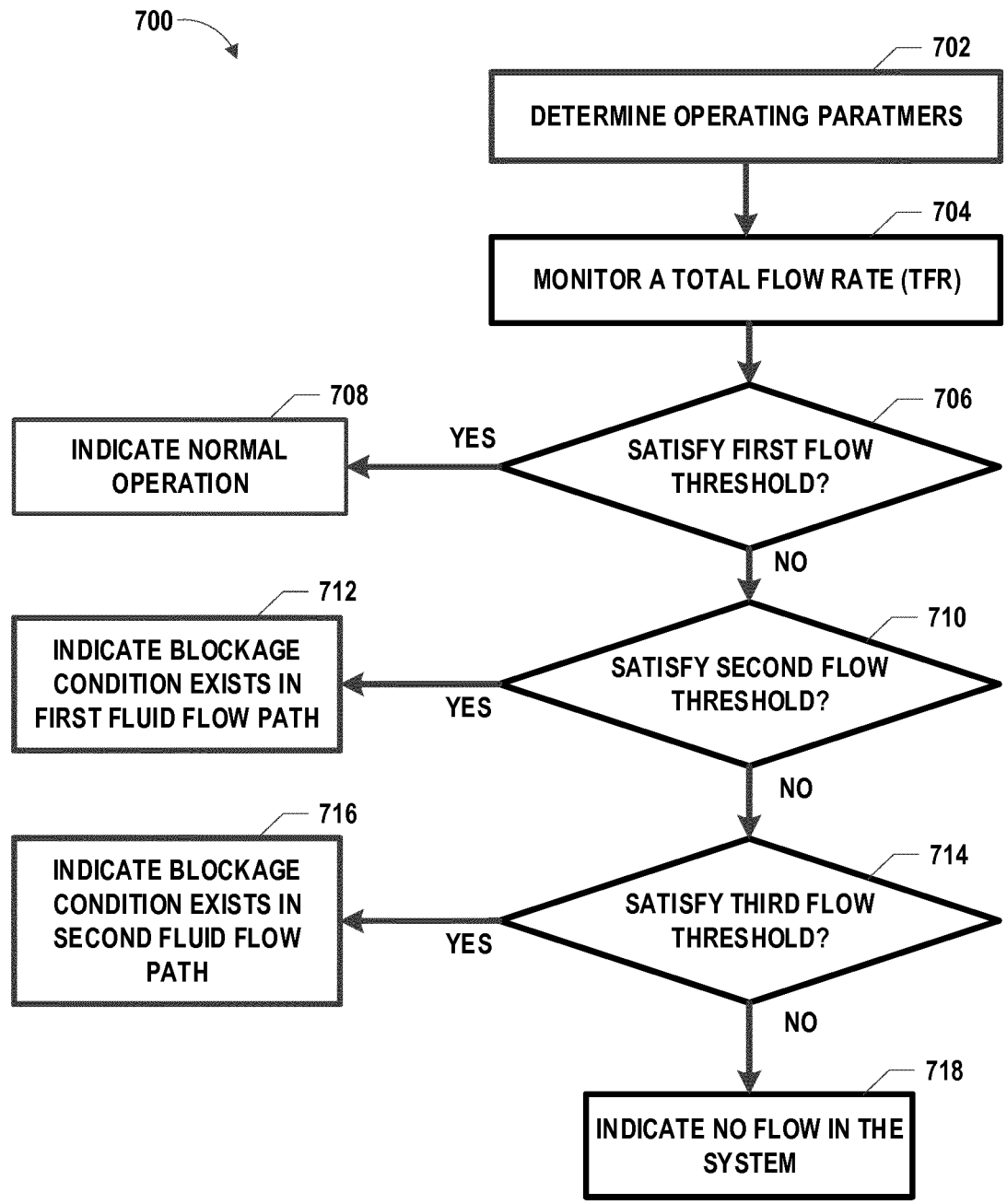
FIG. 7 illustrates a flow diagram of a process for determining and indicating one or more operating conditions according to some embodiments.

FIG. 7 illustrates a flow diagram of a process 700 for determining and indicating one or more operating conditions according to some embodiments. In some embodiments, the process 700 is implemented by reduced pressure wound therapy system 500, such as by one or more controllers of the system.

At block 702, the process 700 determines one or more operating parameters. For example, the process 700 can determine the number of attached wound dressings, whether a fluid flow path corresponding to an attached wound dressings includes an air leak, a leak rate of the one or more air leaks, an expected total flow rate (TFR) of the system, an expected flow rate of each of the fluid flow paths, one or more flow thresholds, a level of activity of the negative pressure source, etc. In some embodiments, the process 600 can perform one or more of such determinations in a calibration mode. Alternatively, some or all of these determinations can be automatically detected or received by the process upon attachment of each wound dressing. In some embodiments, a user can input some or all of the operating parameters or the process can perform internal calculations or can utilize conversion equations or tables.

As described herein, in some embodiments, the process 700 can detect the presence of one or more attached wound dressings by detecting a higher than expected leak rate. For example, the process can automatically detect that a Y-connector is present by detecting a leak higher than the expected leak rate and prompt the user to confirm that another flow path is present. Once the user confirms, the process will determine how to detect a blockage. In other embodiments, the process may detect when a wound dressing is attached and will know the specifications of as air leak based on the attached wound dressing.

The process 700 can also determine an expected flow rate of each of the fluid flow paths corresponding to each of the attached wound dressings. As described herein, each of the fluid flow paths can include one or more air leaks which can be configured to admit fluid into the fluid flow path in which the air leak is located. In addition, each of the air leaks may have a different leak rate (e.g., the rate at which fluid is admitted into the fluid flow path). Accordingly, each of the fluid flow paths can have a different expected flow rate.

Based at least in part on the number of wound dressings or the leak rate of one or more air leaks, the process 700 can determine a plurality of flow thresholds. For example, a process can have two wound dressings, each having a different flow rate. The process can determine a first flow threshold corresponds to a flow rate equal to the aggregation of the expected flow rate of the first fluid flow path and the expected flow rate of the second fluid flow path. A second flow threshold corresponds to the expected flow rate of the second fluid flow path. A third flow threshold corresponds to the expected flow rate of the first fluid flow path. Accordingly, if the monitored TFR satisfies the first flow threshold, then the system is operating normally. If the monitored TFR satisfies the second flow threshold, but not the third flow threshold, then the process can determine that the first fluid flow path is blocked. The process can make this determination because when the flow rate is equal to the expected flow rate of the second fluid flow path, the process is only detecting the flow of the second fluid flow path. As such, the process is not detecting any flow from the first fluid flow path and therefore the process can determine that the first fluid flow path is blocked. In some embodiments, one or more of the thresholds can be higher or lower to than the expected flow rates to, for example, allow for variability during operation.

In some embodiments, the flow thresholds can correspond to the leak rates of the system. For example, a system can have two wound dressings. Each wound dressing can have an associated fluid flow path. The first fluid flow path associated with the first wound dressing includes an air leak of 1 CLP. The second fluid flow path associated with the second wound dressing includes an air leak of 2 CLP. The process 700 can determine a first flow threshold corresponds to a leak rate of 3 CLP, a second flow threshold corresponds to a leak rate of 2 CLP, and a third flow threshold that corresponds to 1 CLP. Accordingly, if the process detects a TFR of 1 CLP (e.g., satisfies the third threshold but does not satisfy the second threshold or third threshold), the process can determine that the second fluid flow path is blocked. The process can make this determination because when TFR is equal to 1 CLP the system is only detecting the flow in the first fluid flow path. As such, the process is not detecting flow from the second fluid flow path and therefore the process can determine that the second fluid flow path is blocked. Similarly, if the process detects TFR of 2 CLP (e.g., TFR satisfies the second threshold and does not satisfy the third threshold), the process can determine that the first fluid flow path is blocked. Likewise, if the process detects TFR of 3 CLP (e.g., TFR satisfies the third threshold), the process can determine that neither the first nor the second fluid flow paths are blocked, and the system is operating normally. Also, if the process detects no flow, the process can determine system blockage due to, for example, all fluid flow paths being blocked or canister being full. This is summarized in the following table:

TABLE 1

| CLPs are 1 and 2 | |
|---|---|
| Flow rate | Determination |
| 3 CLP | Normal operation |
| 2 CLP | First fluid flow path is blocked |

TABLE 1-continued

| CLPs are 1 and 2 | |
|---|---|
| Flow rate | Determination |
| 1 CLP | Second fluid flow path is blocked |
| 0 CLP | System blocked |

In some embodiments, one or more of the thresholds can be higher or lower to account for inaccuracies. For example, although the first air leak is equal to 1 CLP, the first flow threshold provide a small buffer (e.g., 0.03, 0.05, 0.1, 0.15, 0.2, or 0.25 CLP) such that the threshold is slightly below or slightly higher than 1 CLP. Similar buffers can be used for other flow thresholds. For instance, the first and second thresholds can be 0.5 and 1 CLP respectively, and the process can make following determinations:

TABLE 2

| CLPs are 0.5 and 1 | |
|---|---|
| Flow rate | Determination |
| 1.5 CLP | Normal operation |
| 1 CLP | First fluid flow path is blocked |
| 0.5 CLP | Second fluid flow path is blocked |
| 0 CLP | System blocked |

At block 704, the process 700 monitors a total flow rate (TFR) utilizing one or more of the flow rate monitoring techniques described herein. The process can suitably arbitrate between flow rates determined using multiple flow rate monitoring techniques if one or more such techniques are executed in parallel. In certain embodiments, the process can execute one of the techniques, such as the flow rate determination based on the pump speed, and utilize one or more other techniques as needed. In various embodiments, the process can utilize one or more other techniques in cases the determine flow rate is perceived to be inaccurate or unreliable. In some embodiments, the total rate of flow corresponds to an aggregation of the flow of each of the flow path in the process. For example, the total rate of flow can correspond to the aggregation of a flow of the first fluid flow path and a flow of the second fluid flow path.

In some embodiments, the monitored TFR can be compared to an expected TFR to determine if the system is operating normally. Accordingly, by comparing the monitored TFR with the expected TFR (for example, by subtracting the expected TFR from the monitoring TFR), the process 700 can determine a deviation in the current flow rate from the expected flow rate. This deviation can be due to presence of one or more operating conditions.

At block 706, the process 700 determines whether the monitored TFR satisfies (for example, is substantially equal to or exceeds) the first flow threshold, which can correspond to expected TFR. If the first flow threshold is satisfied, then, at block 708, the system can indicate the system is operating normally. Indication in block 708 or in any other block of process 700 can be performed using any of the approaches described herein.

If the monitored TFR does not satisfy the first threshold, the process 700 transitions to block 710, where it determines whether the monitored TFR satisfies the second flow threshold. If the second flow threshold is satisfied (for example, TFR is substantially equal to or is above the second flow threshold), then, at block 712, the process 700 can indicate a blockage condition exists in the first fluid flow path. The process can make this determination because, based upon determining that the TFR satisfies the second threshold (and does not satisfy the first flow threshold), the process can determine it is only detecting flow from the second fluid flow path.

If the monitored TFR does not satisfy the second threshold, the process 700 transitions to block 714, where it determines whether the monitored TFR satisfies the third flow threshold. If the third flow threshold is satisfied (for example, TFR is substantially equal to or is above the third threshold), then, at block 716, the process can indicate a blockage condition exists in the second fluid flow path. The process can make this determination because, based upon determining the TFR satisfies the third threshold (and does not satisfy the first and second thresholds), the process can determine it is only detecting flow from the first fluid flow path.

If the monitored TFR does not satisfy the third threshold, the process 700 transitions to block 718, where it determines and indicate that system is blocked.

While the examples provided in conjunction with the process 700 generally relate to a system having a first and second wound dressing, it should be noted that similar techniques can be performed for a system having any number of wound dressings.

Furthermore, it will be understood that fewer, more, or different blocks can be used as part of the process 700. For example, the process 700 can include fewer blocks if, for instance, one or more leak rates are equal or approximately equal (e.g., +/−0.1 L/min or another suitable deviation). As described above, a system can have two wound dressings and each wound dressing can have an associated fluid flow path. For example, the first fluid flow path associated with the first wound dressing can include an air leak of 1 CLP, and the second fluid flow path associated with the second wound dressing can also include an air leak of 1 CLP. Accordingly, the process 700 can utilize two flow thresholds: a first flow threshold corresponding to a leak rate of 2 CLP, and a second flow threshold corresponding to a leak rate of 1 CLP. If the process 700 detects a TFR of 1 CLP (e.g., satisfies the first threshold but does not satisfy the second threshold), the process can determine that either the first or second fluid flow path is blocked. The process 700 can make this determination because when TFR is equal to 1 CLP, the process is only detecting the flow from one of the fluid flow paths. In some cases, the process can determine or indicate which fluid flow path is blocked, while in other cases, the process can determine or indicate that a blockage has occurred somewhere in one of the fluid flow paths. If the process 700 detects TFR of 2 CLP (e.g., TFR satisfies the second threshold), the process can determine that neither the first nor the second fluid flow paths are blocked, and the system is operating normally. Also, if the process detects no flow, the process can determine system blockage due to, for example, all fluid flow paths being blocked or canister being full. This is summarized in the following table:

TABLE 3

| CLPs are 1 and 1 | |
| --- | --- |
| Flow rate | Determination |
| 2 CLP | Normal operation |
| 1 CLP | Blockage occurred somewhere in the fluid flow paths |
| 0 CLP | System blocked |

Figure 8:
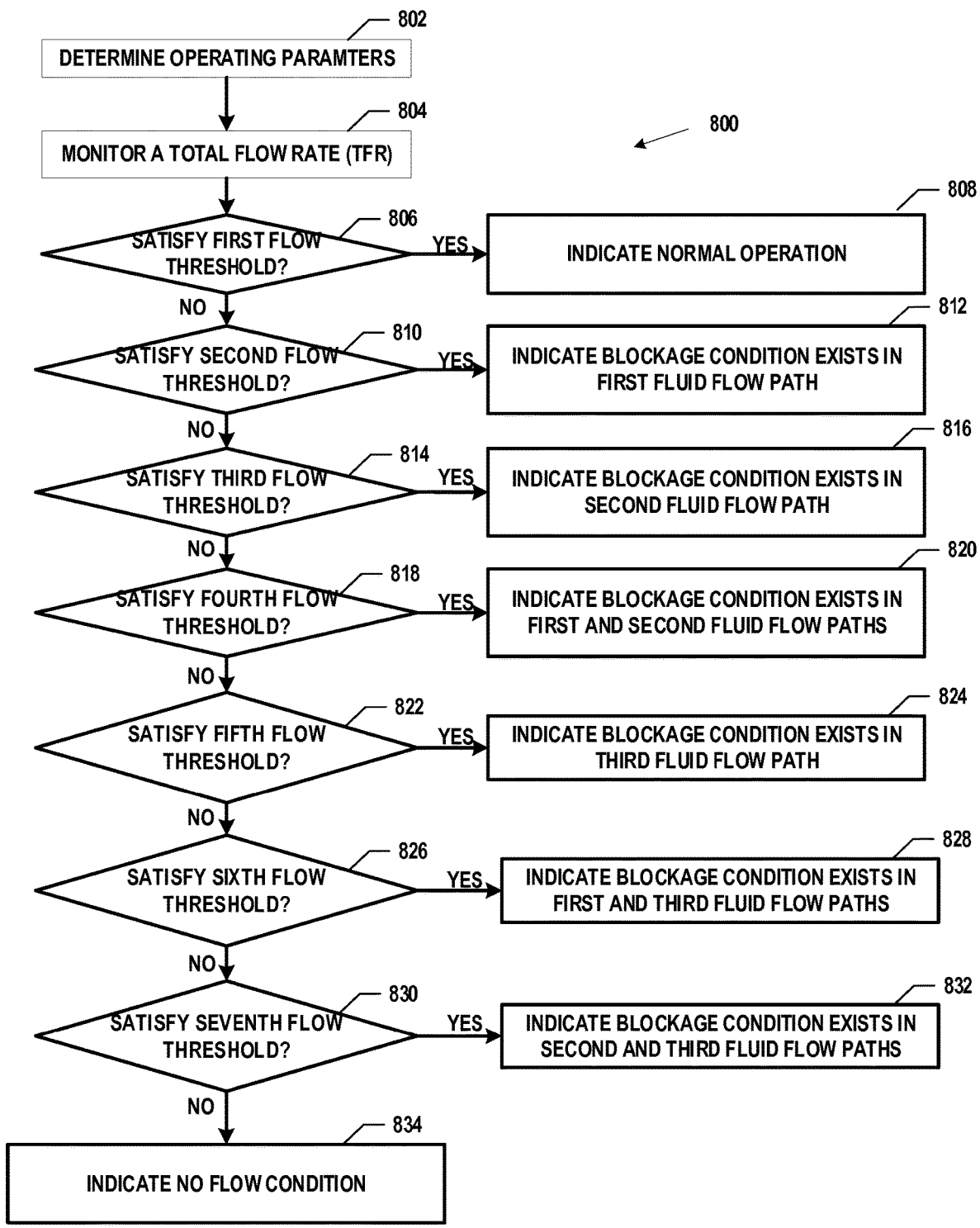
FIG. 8 illustrates a flow diagram of a process for determining and indicating one or more operating conditions according to some embodiments.

FIG. 8 illustrates a flow diagram of a process 800 for determining and indicating one or more operating conditions according to some embodiments. In some embodiments, the process 800 is implemented by reduced pressure wound therapy system 600, such as by one or more controllers of the system.

At block 802, similar to what is described with reference to block 702 of FIG. 7, the process 800 determines one or more operating parameters. For example, the process can determine the number of attached wound dressings, whether a fluid flow path corresponding to an attached wound dressings includes an air leak, a leak rate of the one or more air leaks, a total leak rate, an expected total flow rate (TFR) of the system, an expected flow rate of each of the fluid flow paths, one or more flow thresholds, a level of activity of the pump, etc. In some embodiments, the process can perform some or all of these determinations in calibration mode. Alternatively, some or all of these operating parameters can be automatically detected or received by the process upon attachment of each wound dressing. In some embodiments, a user can input some or all of the operating parameters or the process can perform internal calculations or can utilize conversion equations or tables.

As described herein, the process 800 may detect the presence of one or more attached wound dressings by detecting a higher than expected leak rate. For example, the process can automatically detect that a W-connector is present by detecting a leak higher than the expected leak rate and prompt the user to confirm that another flow path is present. Once the user confirms, the process will know how to detect a blockage. In other embodiments, the process may detect when a wound dressing is attached and will know the specifications of as air leak based on the attached wound dressing.

The process 800 can determine a plurality of flow thresholds. In this example, the process can determine at least seven flow thresholds. However, it should be noted that more or fewer flow thresholds can be determined. As described with respect to block 702 of FIG. 7, the flow thresholds can correspond to TFR of the system in presence of one or more operating conditions.

In some embodiments, a first flow threshold corresponds to a flow rate equal to the aggregation of an expected flow rate of the first fluid flow path (expected first flow rate), the expected flow rate of the second fluid flow path (expected second flow rate), and the expected flow rate of the third fluid flow path (expected third flow rate). A second flow threshold corresponds to a flow rate equal to the aggregation of the expected second flow rate and the expected third flow rate. A third flow threshold corresponds to a flow rate equal to the aggregation of the expected first flow rate and the expected third flow rate. A fourth flow threshold corresponds to a flow rate equal to the aggregation of the expected first flow rate and the expected second flow rate. A fifth flow threshold corresponds to a flow rate equal to the expected third flow rate. A sixth flow threshold corresponds to a flow rate equal to the expected second flow rate. A seventh flow threshold corresponds to a flow rate equal to the expected first flow rate.

For example, the first fluid flow path can have a leak rate of 1 CLP, the second fluid flow path can have a leak rate of 3 CLP, and the third fluid flow path can have a leak rate of 5 CLP. A first flow threshold corresponds to a leak rate equal 9 CLP (e.g., an aggregation of all of the leak rates). A second flow threshold corresponds to a leak rate equal to 8 CLP. A third flow threshold corresponds to a leak rate equal to 6 CLP. A fourth flow threshold corresponds to a leak rate equal to 5 CLP. A fifth flow threshold corresponds to a leak rate equal to 4 CLP. A sixth flow threshold corresponds to a leak rate equal to 3 CLP. A seventh flow threshold corresponds to a leak rate equal to 1 CLP. This is summarized as follows:

TABLE 4

CLPs are 1, 3 and 5

| Flow rate | Determination |
|---|---|
| 9 CLP | Normal operation |
| 8 CLP | First fluid flow path is blocked |
| 7 CLP | N/A or unexpected flow rate |
| 6 CLP | Second fluid flow path is blocked |
| 5 CLP | First and second fluid flow paths are blocked |
| 4 CLP | Third fluid flow path is blocked |
| 3 CLP | First and third fluid flow paths are blocked |
| 2 CLP | N/A or unexpected flow rate |
| 1 CLP | Second and third fluid flow paths are blocked |
| 0 CLP | System blocked |

In some embodiments, order of the flow thresholds may change based on the leak rate of the air leaks.

At block 804, similar to what is described with reference to block 704 of FIG. 7, the process 800 monitors a TFR utilizing one or more of the flow rate monitoring techniques described herein.

At block 806, the process 800 determines whether the monitored TFR satisfies (for example, is substantially equal to or exceeds) the first flow threshold. If the first flow threshold is satisfied, then, at block 808, the process can indicate the system is operating normally. Indication in block 808 or in any other block of process 800 can be performed using any of the approaches described herein.

If the monitored TFR does not satisfy the first flow threshold, the process transitions to block 810, it determines whether the monitored TFR satisfies (for example, is substantially equal to or exceeds) the second flow threshold. If the second flow threshold is satisfied (and the first flow threshold is not satisfied), then, at block 812, the process can indicate a blockage condition exists in the first fluid flow path. The process can make this determination because, based on the satisfied threshold, the process can determine it is only detecting flow from the second and third fluid flow paths.

If the monitored TFR does not satisfy the second flow threshold, the process transitions to block 814, where it determines whether the monitored TFR satisfies (for example, is substantially equal to or exceeds) the third flow threshold. If the third flow threshold is satisfied (and the first and second flow thresholds are not satisfied), then, at block 816, the process can indicate a blockage condition exists in the second fluid flow path. The process can make this determination because, based on the satisfied threshold, the process can determine it is only detecting flow from the first and third fluid flow paths.

If the monitored TFR does not satisfy the third flow threshold, the process transitions to block 818, where it determines whether the monitored TFR satisfies (for example, is substantially equal to or exceeds) the fourth flow threshold. If the fourth flow threshold is satisfied (and the first, second, and third flow thresholds are not satisfied), then, at block 820, the process can indicate a blockage condition exists in the first and second fluid flow paths. The process can make this determination because, based on the satisfied threshold, the process can determine it is only detecting flow from the third fluid flow path.

If the monitored TFR does not satisfy the fourth flow threshold, the process transitions to block 822, where it determines whether the monitored TFR satisfies (for example, is substantially equal to or exceeds) the fifth flow threshold. If the fifth flow threshold is satisfied (and the first through fourth flow thresholds are not satisfied), then, at block 824, the process can indicate a blockage condition exists in the third fluid flow path. The process can make this determination because, based on the satisfied threshold, the process can determine it is only detecting flow from the first and second fluid flow paths.

If the monitored TFR does not satisfy the fifth flow threshold, the process transitions to block 826, where it determines whether the monitored TFR satisfies (for example, is substantially equal to or exceeds) the sixth flow threshold. If the sixth flow threshold is satisfied (and the first through fifth flow thresholds are not satisfied), then, at block 828, the process can indicate a blockage condition exists in the first and third fluid flow paths. The process can make this determination because, based on the satisfied threshold, the process can determine it is only detecting flow from the second fluid flow path.

If the monitored TFR does not satisfy the sixth flow threshold, the process transitions to block 830, where it determines whether the monitored TFR satisfies (for example, is substantially equal to or exceeds) the seventh flow threshold. If the seventh flow threshold is satisfied (and the first through sixth flow thresholds are not satisfied), then, at block 832, the process can indicate a blockage condition exists in the second and third fluid flow paths. The process can make this determination because, based on the satisfied threshold, the process can determine it is only detecting flow from the first fluid flow path.

At block 834, the process 800 determines that no flow thresholds are satisfied, and indicates system blocked condition.

While the examples provided in conjunction with process 800 relate to a system having a first, second and third wound dressings, it should be noted that similar techniques can be performed for a system having any number of wound dressings.

Figure 9A:
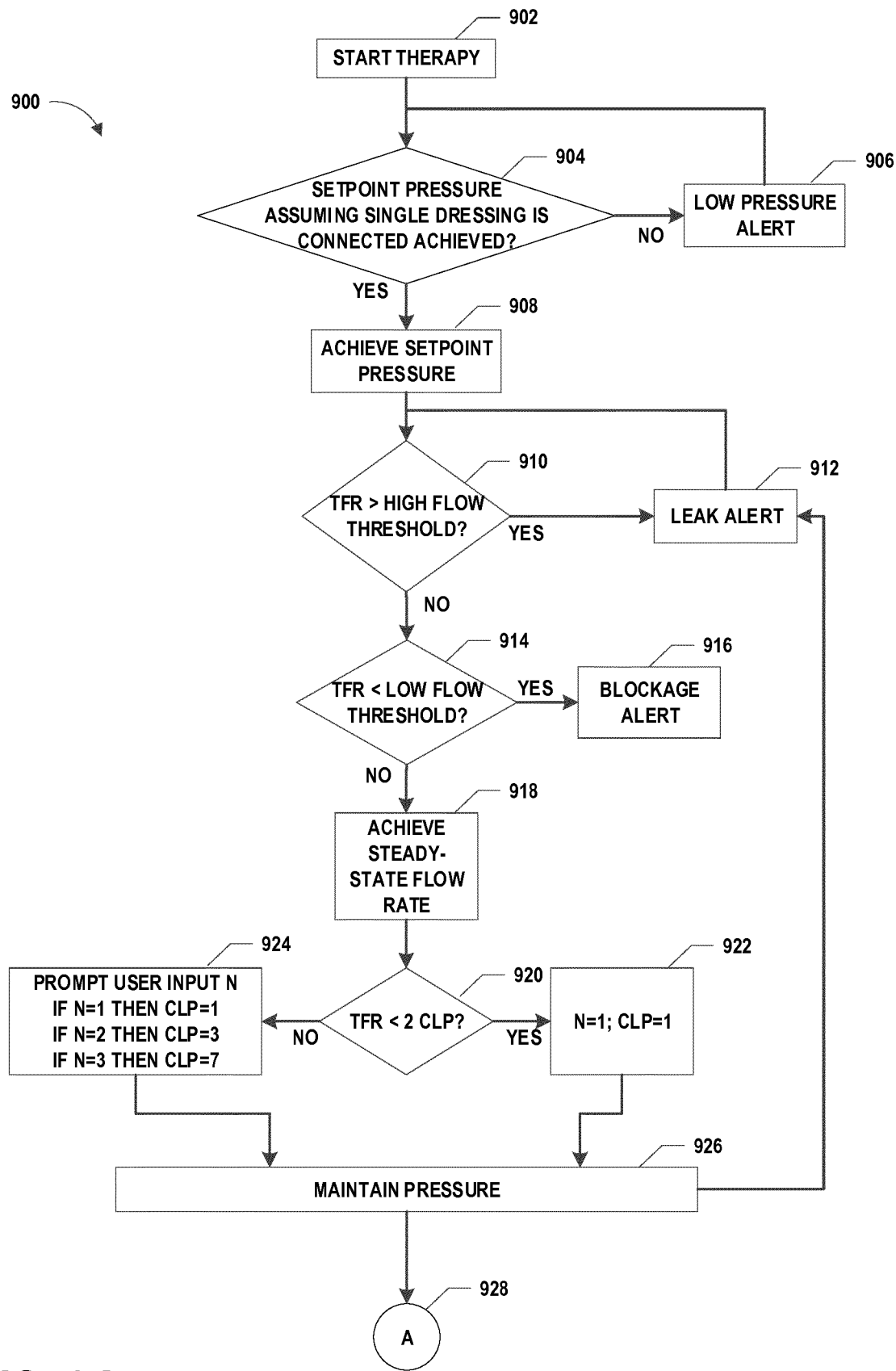
FIGS. 9A-9B illustrate a flow diagram of a process for determining and indicating one or more operating conditions according to some embodiments.
Figure 9B:
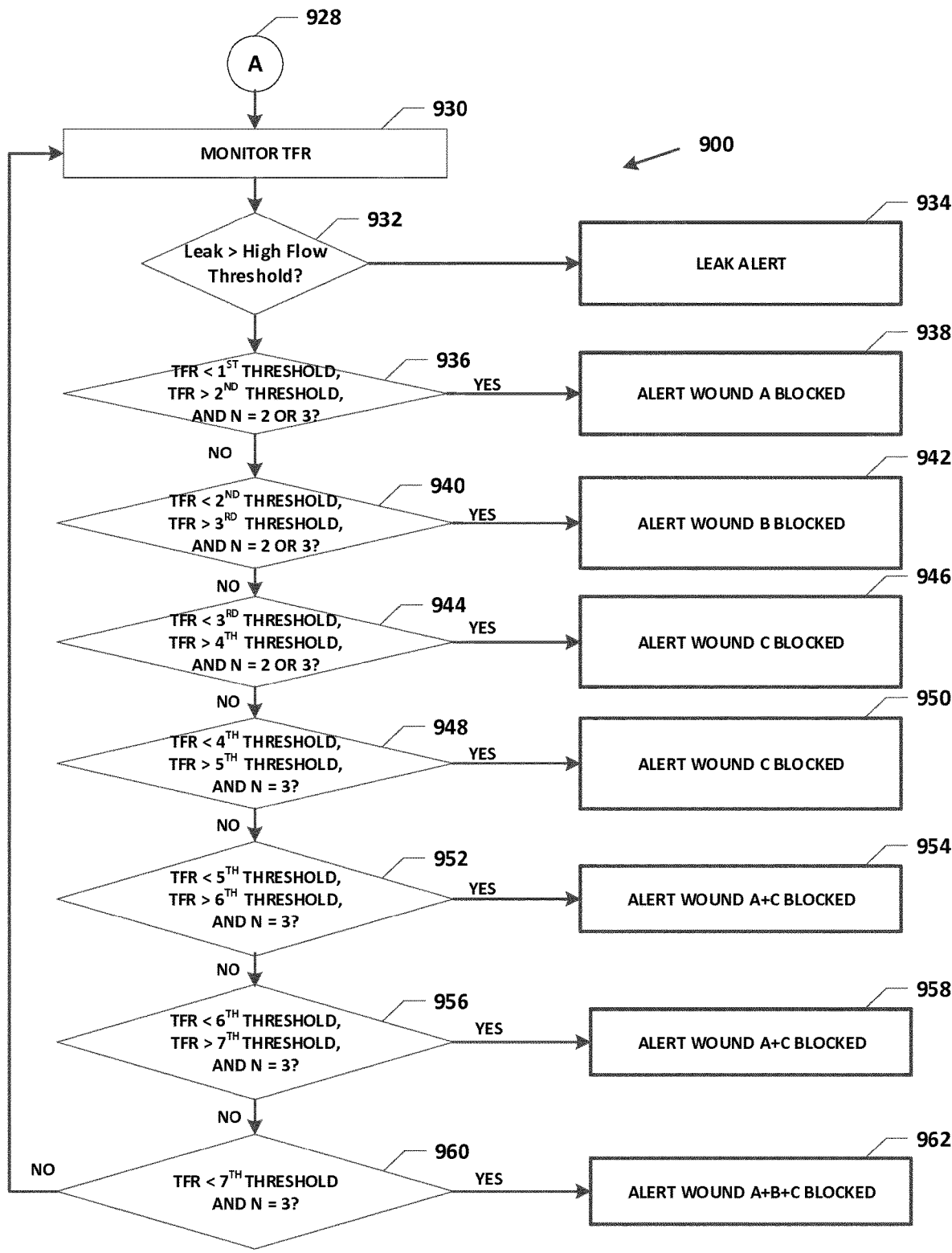

FIGS. 9A-9B illustrate a flow diagram of a process 900 for determining and indicating one or more operating conditions according to some embodiments. In some embodiments, the process 900 is implemented by reduced pressure wound therapy system 600, such as by one or more controllers of the system. The process 900 can be implemented on a system having one, two, or three wound dressings. In embodiment corresponding to FIGS. 9A-9B, a first flow path connected to a first wound dressing includes a leak of 1 CLP, a second fluid flow path connected to a second wound dressing includes a leak of 2 CLP, and a third fluid flow path connected to a third wound dressing includes a leak of 4 CLP. In other embodiments, one or more of air leak rates can be different.

At block 902, negative pressure therapy is initiated. For instance, the pump may be transitioned from a standby, manual pause, or deactivated state into an active state. In some embodiments, negative pressure therapy can be initiated manually, such as through user input (for example, via a signal received from the button 212b). Alternatively or in addition, the pump may automatically transition into an active state, for example, after expiration of a set period of time.

In some embodiments, at this stage in the process 900, the process has not determined the number of attached wound dressings. For example, one, two, or three wound dressings could be attached, but the process 900 assumes that a single wound dressing is connected via a flow path including a threshold air leak, such as about 1 CLP or another suitable leak rate. Accordingly, at block 904, the process 900 checks to ensure that the system has achieved target negative pressure in the presence assuming that only a single wound dressing with a threshold leak rate is connected. Achieving target negative pressure can be associated with obtaining setpoint pressure at the wound. If the target negative pressure has not been achieved, the process 900 determines that the negative pressure is low (due to, for example, a leak in the dressing or the interface between the dressing and the wound) and transitions to block 906, where it provides an indication to a user, for instance, via a low pressure (or leak) alert or alarm. The alarm can indicate to the patient or medical professional, such as a doctor or nurse, that there may be a problem with achieving a reliable seal. The process 900 can transition to block 906 in response to comparing pressure at the wound (for example, measured with a pressure sensor) to a first low pressure, leak, or high flow threshold. This comparison can be performed over a period of time. If pressure at the wound does not achieve at least pressure associated with the first high flow threshold, the process 900 can transition to block 906 and indicate presence of a leak. If target negative pressure is achieved, the process can transition to block 908. Target negative pressure can be any suitable pressure setpoint as described herein.

After achieving the setpoint, the process 900 transitions to block 910, in which the process can determine the TFR and use the TFR to determine if there is a leak or a blockage. For determining high flow or leak, the process 900 can use a second high flow threshold, which can be different from the first high flow threshold. As the process has not determined the number of connected dressing and the total leak rate in the system associated with the flow paths connecting the dressing, the second high flow threshold can be the approximately equal to an expected flow rate of a system having a maximum number of connected wound dressings. For instance, a system configured to support at most three wound dressings with flow paths including leak rates of 1 CLP, 2 CLP, and 4 CLP can have a second high flow threshold of about 7 CLP. In some embodiments, one or more of the thresholds can be higher or lower to than the expected flow rates to, for example, allow for variability during operation.

In some embodiments, the process 900 can also determine whether the TFR is greater than a second high flow threshold, which can correspond to a second low pressure, leak, or high flow threshold. Second high flow threshold may be different than the first high flow threshold. For example, second high flow threshold may be higher (or lower) than the first high flow threshold to tolerate higher flow in the system. This difference in flow thresholds can be due to the assumption that once a reliable seal has been achieved (when the process transitioned into block 908), the medical professional is no longer present near the patient to address any issues with the seal. Because of this, the second high flow threshold may be less sensitive than the first high flow threshold, which can result in the system tolerating higher leak rates after achieving target negative pressure.

In block 910, if the process determines that the TFR is greater than the second high flow threshold, the process determines that a leak is present in the system and the process 900 transitions to block 912, where it provides an indication to a user, for instance, via a leak alert or alarm. The process can continue to provide a leak alert until maintenance has been performed. Alternatively or in addition, the process 900 can transition to block 910 to continuously check whether a leak condition exists.

If no leak is detected, the process 900 can transition to block 914, where the process 900 checks whether there is blockage in the system. In some embodiments, the process determines if the TFR is below a low flow threshold. As mentioned herein, the process has not yet have determined the number of attached wound dressings. The process can assume that a single wound dressing is connected including a threshold air leak, such as about 1 CLP or another suitable leak rate. If low flow threshold has not been achieved or satisfied (for example, TFR is below the low flow threshold), the process determines that a blockage exists. The process 900 transitions to block 916, where it provides an indication to a user, for instance, via a blockage alert or alarm.

If the low flow threshold has been achieved, then the process 900 can transition to block 918, where it determines that a steady-state flow rate is achieved. The process can record the steady-state flow rate for later use.

The process 900 can transition to blocks 920, 922, and 924 where the process determines the number of connected wound dressings. In some embodiments, the process determines whether the TFR is less than the leak rate of the second flow path connecting the second wound dressing (block 920). For instance, in some embodiments, the leak rate of the second flow path corresponds to 2 CLP. Accordingly, if the TFR does not satisfy the leak rate of the second flow path (e.g., less than 2 CLP), then the process can determine that only a single wound dressing is connected (block 922). In some embodiments, the process has initially determined how many wound dressings are connected, but the expected flow rates of one or more wound dressings are attached are known a piori. As such, at block 922, the process can determine that one dressing is connected (e.g., N=1) and set the expected TFR to about 1 CLP (e.g., CLP=1).

In block 920, if the TFR exceeds (for example, is greater than or equal to) the expected leak rate of the second wound dressing (e.g., greater than or equal to 2 CLP), the process 900 can determine that more than one wound dressing is connected. The process can transition to block 924, where it prompts a user to provide the number of connected dressings. For example, a user can provide that 1 dressing is connected (e.g., N=1), two dressings are connected (e.g., N=2), or three dressings are connected (e.g., N=3). The user can also provide the leak rates (or CLPs) included in the flow paths associated with the connected wound dressings. In some embodiments, instead of prompting the user to provide information on connected wound dressings, the process 900 can determine this automatically without user interaction by comparing the TFR to a set of flow thresholds corresponding to the expected flow associated with different combinations of connected wound dressings.

The process 900 can transition to block 926, where it continues to maintain negative pressure by operating the negative pressure source.

With reference to FIG. 9B, the process 900 can transition to block 930 where it monitors the TFR. Similar to what is described with reference to blocks 806-834 of FIG. 8, the process can determine whether the monitored TFR or leak rate satisfies one or more flow thresholds.

For example, the first fluid flow path can have a leak rate of 1 CLP, the second fluid flow path can have a leak rate of 2 CLP, and the third fluid flow path can have a leak rate of 4 CLP. A first flow threshold corresponds to a leak rate equal 7 CLP (e.g., an aggregation of all of the leak rates). A second flow threshold corresponds to a leak rate equal to 6 CLP. A third flow threshold corresponds to a leak rate equal to 5 CLP. A fourth flow threshold corresponds to a leak rate equal to 4 CLP. A fifth flow threshold corresponds to a leak rate equal to 3 CLP. A sixth flow threshold corresponds to a leak rate equal to 2 CLP. A seventh flow threshold corresponds to a leak rate equal to 1 CLP. This is summarized as follows:

TABLE 5

CLPs are 1, 2 and 4

| Flow Threshold | Flow rate | Determination or Indication |
|---|---|---|
| 1st | 7 CLP | Normal operation |
| $2^{nd}$ | 6 CLP | First fluid flow path is blocked |
| $3^{rd}$ | 5 CLP | Second fluid flow path is blocked |
| $4^{th}$ | 4 CLP | First and second fluid flow paths are blocked |
| $5^{th}$ | 3 CLP | Third fluid flow path is blocked |
| $6^{th}$ | 2 CLP | First and third fluid flow paths are blocked |
| $7^{th}$ | 1 CLP | Second and third fluid flow paths are blocked |
|  | 0 CLP | System blocked |

In some embodiments, order of the flow thresholds may change based on the leak rate of the air leaks.

At block 930, the process 900 can determine a leak rate. In some embodiments, the leak rate is determined from the following formula:

$$Leak = TFR - CLP$$

wherein TFR is total flow rate of the system, CLP is total expected CLP of the system, and Leak is the total leak rate of the system (excluding the leak rates included in the flow paths). The process 900 can use the leak rate to determine one or more operating conditions. For example, the process can determine blockages in one or more flow paths associated with the one or more connected wound dressings.

In block 932, the process can determine if the leak is greater than a high flow threshold (for example, the second high flow threshold). If this condition is satisfied, then the process 900 can transition to block 934 and provide a leak alert (similar to the leak alert of block 912). In some embodiments, because detection of leak or high flow has already been performed in block 910, the process may not perform block 932.

At block 936, the process 900 can determine (1) whether the monitored TFR or leak rate is less than the first flow threshold and (2) whether the monitored TFR or leak rate is greater than or equal to the second flow threshold. If the TFR is less than the first threshold and is greater than or equal to the second threshold, then, at block 938, the process 900 can indicate a blockage condition exists in the first fluid flow path (e.g., $1^{st}$ wound dressing is blocked). The process can make this determination because, based on the thresholds, the process can determine it is only detecting flow from the second and third fluid flow paths.

If the monitored TFR or leak rate does not satisfy (for example, is less than) the second flow threshold, the process 900 can transition to block 940, where it determines whether the monitored TFR or leak rate satisfies (for example, is substantially equal to or exceeds) the third flow threshold. If the third flow threshold is satisfied (and the second flow threshold is not satisfied), then, at block 942, the process can indicate a blockage condition exists in the second fluid flow path (e.g., $2^{nd}$ wound dressing is blocked). The process can make this determination because, based on the thresholds, the process can determine it is only detecting flow from the first and third fluid flow paths.

If the monitored TFR or leak rate does not satisfy the third flow threshold, the process can transition to block 944, where it determines whether the monitored TFR or leak rate satisfies (for example, is substantially equal to or exceeds) the fourth flow threshold. If the fourth flow threshold is satisfied (and the third flow threshold is not satisfied), then, at block 946, the process can indicate a blockage condition exists in the first and second fluid flow paths. The process can make this determination because, based on the thresholds, the process can determine it is only detecting flow from the third fluid flow path.

If the monitored TFR or leak rate does not satisfy the fourth flow threshold, the process can transition to block 948, where it determines whether the monitored TFR or leak rate satisfies (for example, is substantially equal to or exceeds) the fifth flow threshold. If the fifth flow threshold is satisfied (and the fourth flow threshold is not satisfied), then, at block 950, the process can indicate a blockage condition exists in the third fluid flow path (e.g., the $3^{rd}$ wound dressing is blocked). The process can make this determination because, based on the thresholds, the process can determine it is only detecting flow from the first and second fluid flow paths.

If the monitored TFR or leak rate does not satisfy the fifth flow threshold, the process can transition to block 952, where it determines whether the monitored TFR or leak rate satisfies (for example, is substantially equal to or exceeds) the sixth flow threshold. If the sixth flow threshold is satisfied (and the first through fifth flow thresholds are not satisfied), then, at block 954, the process can indicate a blockage condition exists in the first and third fluid flow paths. The process can make this determination because, based on the thresholds, the process can determine it is only detecting flow from the second fluid flow path.

If the monitored TFR or leak rate does not satisfy the sixth flow threshold, the process can transition to block 956, where it determines whether the monitored TFR or leak rate satisfies (for example, is substantially equal to or exceeds) the seventh flow threshold. If the seventh flow threshold is satisfied (and the sixth flow threshold is not satisfied), then, at block 958, the process can indicate a blockage condition exists in the second and third fluid flow paths. The process can make this determination because, based on the satisfied threshold, the process can determine it is only detecting flow from the first fluid flow path.

If the monitored TFR or leak rate does not satisfy the seventh flow threshold, the process can transition to block 962, where it can indicate a blockage condition exists in all of the fluid flow paths. The process can make this determination because, based on the satisfied threshold, the process can determine it is not detecting flow from any of the first, second or third fluid flow paths.

One or more indications, alerts, or alarms described in connection with FIGS. 9A-9B can be provide any of the indications, alarms or alerts described herein. While the examples provided in conjunction with process 900 relate to a system having a first, second and third wound dressings, it should be noted that similar techniques can be performed for a system having any number of wound dressings.

Graphical User Interfaces

In some embodiments, the pump assembly 230 can be operated using a touchscreen interface displayed on the screen 206. In addition or alternatively, one or more displays can be in wired or wireless communication with a pump assembly. The display(s) can be configured to render a number of screens or graphical user interfaces (GUIs) to, for example, configure, control or monitor the operation of the TNP system. The touchscreen interface can be actuated or operated by a finger (or a stylus or another suitable device). Tapping the touchscreen can result in making a selection. To scroll, a user can touch the screen and hold and drag to view the selections. Additional or alternative ways to operate the touchscreen interface can be implemented, such as multiple finger swipes for scrolling, multiple finger pinch for zooming, and the like.

FIGS. 10A-10D illustrate GUI screens of a TNP system, according to some embodiments. The illustrated GUI screens can be used with any of the embodiments of TNP systems described herein. For example, the GUI screens can be displayed on the screen 206, which can be configured as a touchscreen interface. Information displayed in the GUIs can be generated based on input received from the user. The GUIs can be utilized for initializing the device, selecting and adjusting therapy settings, monitoring device operation, uploading data to the network (e.g., cloud), and the like. The illustrated GUIs can be generated directly by an operating system running on the processor 310 and/or by a GUI layer or component running on the operating system. For instance, the screens can be developed using Qt framework available from Digia.

Figure 10A:
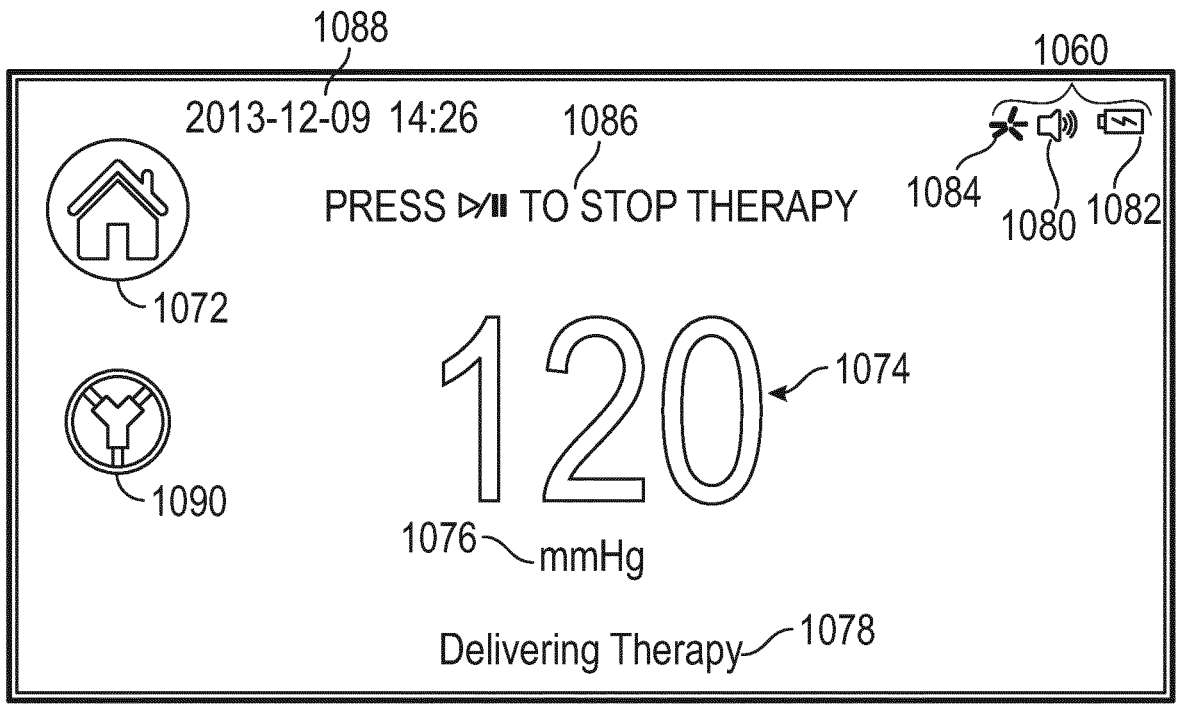
FIGS. 10A-10D illustrate graphical user interfaces (GUIs) of a topical negative pressure (TNP) system, according to some embodiments.

FIG. 10A illustrates therapy delivery GUI, according to some embodiments. As described herein, a TNP system can include a Y-, W-, or other connector for treating multiple wounds (e.g., two, three, or more wounds) with pump assembly 230. The GUI of FIG. 10A can be accessed by initiating therapy, such as by pressing the button 212b. As is illustrated, label 1078 ("Delivering Therapy") indicates that continuous therapy at −120 mmHg of reduced pressure (label 1074) is being delivered to a wound.

The therapy delivery GUI can include a status bar 1060 that includes icons indicating operational parameters of the device. Animated icon 1084 can be a therapy delivery indicator. For example, when therapy is not being delivered, icon 1084 can be static and displayed in a color, such as gray. When therapy is being delivered, icon 1084 can turn a different color, such as orange, and become animated. For example, icon 1084 can rotate, pulsate, become filled with color, etc. In the illustrated example, icon 1084 is an energy burst having multiple petals, and the animation sequences through the petals becoming filled with orange color. However, any other suitable animation or combination of animations can be used.

Other status bar icons 1060 include a volume indicator 1082 and a battery indicator 1080, and may include additional icons, such as wireless connectivity. The therapy delivery GUI can include date/time and information 1088. Message 1086 indicates that therapy settings can be stopped or paused by pressing a button, such as button 212b, on the pump assembly 230. Menu item 1072 can be configured to return to a therapy settings screen or home screen. Additional or alternative controls, indicators, messages, icons, and the like can be used.

In some embodiments, the pump assembly 150 can include visual, audible, tactile, haptic, or other types of indicators or alarms configured to signal to the user various operating conditions. For example, an indicator or alarm can indicate one or more of a blockage condition, a system blocked condition, or a normal operation condition.

The operation condition indicator can be a visual indicator that can dynamically change in shape, color, content or the like in response to a change in operating condition. For example, in the illustrated embodiment, the GUI includes an animated Y-connector icon 1090. In some cases, the animated Y-connector icon 1090 of the GUI can correspond to the physical appearance of a dressing or connector such that a user can identify, based on the animated Y-connector icon 1090 and the physical appearance of the dressing or connector, which, if any, dressings or branches are blocked. This link between the animated Y-connector icon 1090 and a physical indicator of the affected dressing can advantageously minimize the number of cognitive steps for a user to follow in order to identify the affected dressing.

The presence of the animated Y-connector icon 1090 on the GUI can indicate that a Y-connector is connected to the TNP apparatus and/or is providing treatment to one or more wounds. In addition or alternatively, when a Y-connector is not connected, animated Y-connector icon 1090 can be static and displayed in a color, such as gray. In contrast, when a Y-connector is not connected, animated Y-connector icon 1090 can be animated and displayed in a color, such as no color, green, or yellow.

The GUI can indicate an operating condition of the TNP system using the animated Y-connector icon 1090. For example, to indicate a normal operating condition (or a no-alarm condition), the GUI may provide arrows moving through each branch of the animated Y-connector icon 1090 to indicate fluid flow through those branches. In addition or alternatively, the animated Y-connector icon 1090 can be color-coded to indicate a normal operating condition. For example, a first color, such as no color or a green color, can indicate the normal operating condition. Additional or alternative animations, indicators, or the like can be used to indicate a normal operating condition.

As another example, GUI can utilize the animated Y-connector icon 1090 to indicate a blockage condition or a system blocked condition. For instance, the GUI may illustrate a stationary arrow and/or an "x" at a blocked branch to indicate that branch is blocked. In addition or alternatively, the GUI can color code the animated Y-connector icon 1090 to indicate a blockage condition. For example, a first color (e.g., yellow) can indicate a branch is blocked. In some cases, the color of the blockage condition can correspond to the color(s) corresponding to the International Electrotechnical Commission (IEC) 60601-8 alarms standard. Additional or alternative controls, indicators, messages, icons, and the like can be used. For example, similar indicators could be utilized for a W-shaped or other connector.

In some cases, based at least in part on a flow rate of one or more fluid flow paths, the system can detect a presence of blood in the system. In response, the system can provide visual, audible, tactile, haptic, or other types of indicators or alarms configured to signal to the user the detection of blood. For example, the system can include a physical indicator such as an LED on each fluid flow path. Based on a detection of blood in a flow path, the system can activate or deactivate the LED. For example, a high priority indicator or alarm can include an LED flashing or activated at a first color (e.g., red), a medium priority indicator or alarm can include the LED flashing or activate at a second color (e.g., yellow), and during normal conditions the LED can be activated or deactivated.

In addition or alternatively, the system can utilize the GUI to signal to the user the detection of blood. For example, the GUI can present a label (e.g., "Please check for blood in path B") that indicates that blood has been detected in a fluid flow path. Additional or alternative labels or messages can be used. As another example, the GUI can utilize the animated Y-connector icon 1090 to indicate blood detection. For instance, the GUI can present a colored (e.g., red) indicator on the animated Y-connector icon 1090 to indicate the presence of blood. Similarly, to indicate the presence of blood on a particular fluid flow path, the GUI may present arrows moving through a branch of the animated Y-connector icon 1090. In some cases, the arrow can be a different color than arrows presented during normal operation. Similarly, the GUI can alter a color of at least a portion of a branch of the animated Y-connector icon 1090 to indicate that the branch includes blood. For example, the GUI can turn the branch red. Additional or alternative controls, indicators, messages, icons, and the like can be used to indicate blood detection.

Figure 10B:
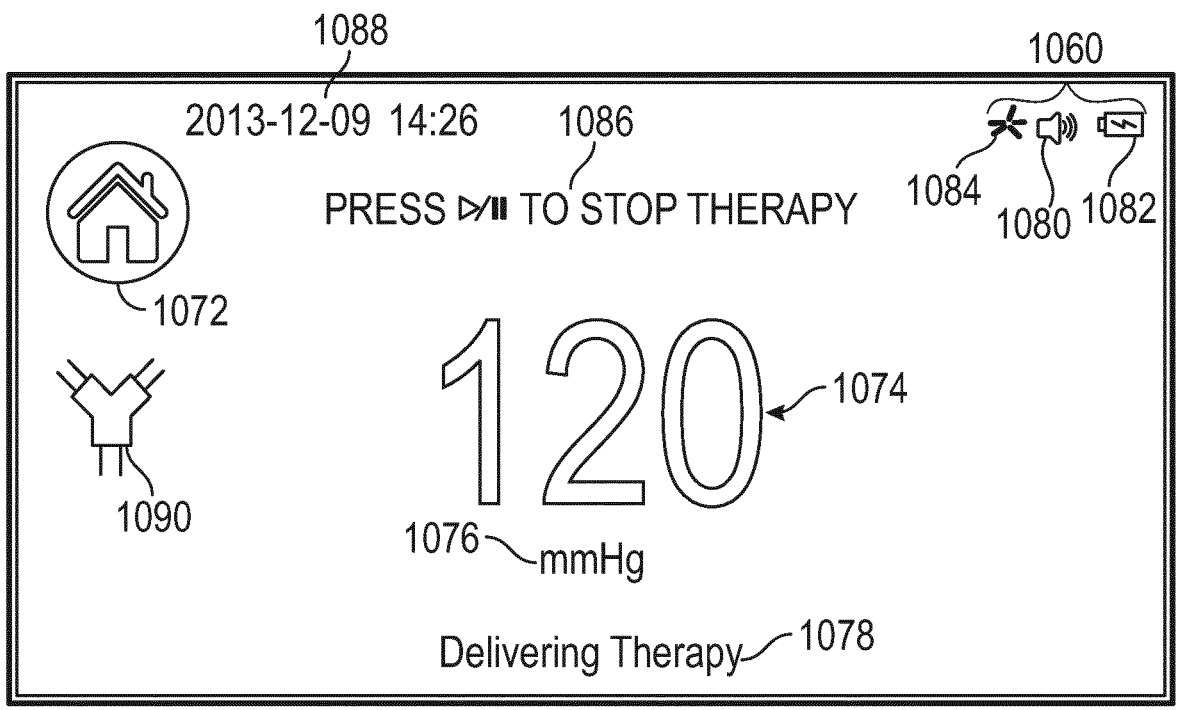
Figure 10C:
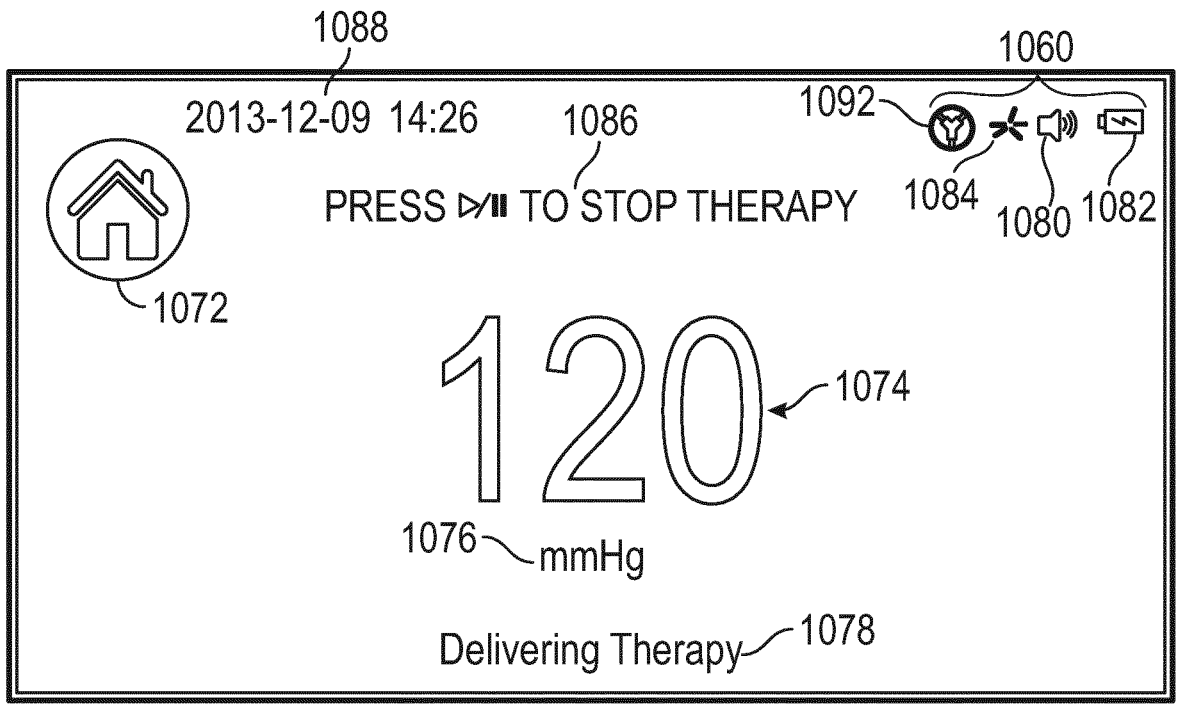
Figure 10D:
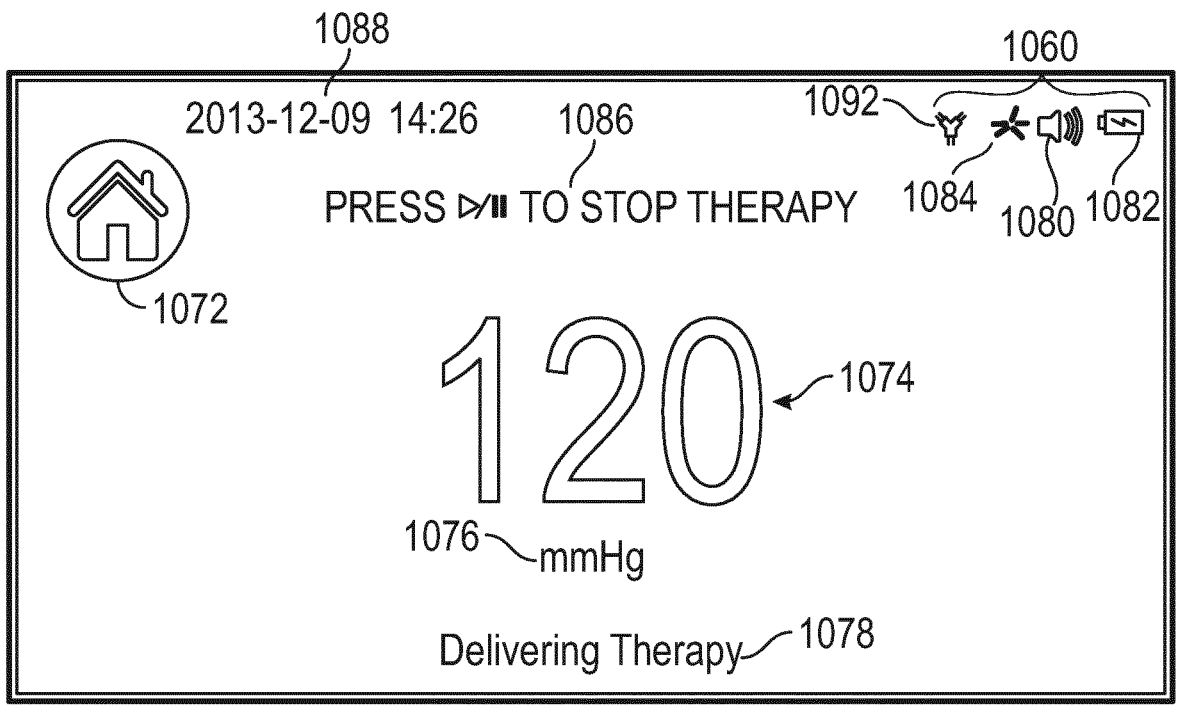

FIG. 10B illustrates another example of animated Y-connector icon 1090. However, additional or alternative controls, indicators, messages, icons, and the like can be used. Furthermore, in some cases, as illustrated in FIGS. 10C and 10D, an animated Y-connector icon 1092 can be additionally or alternatively included as a status bar icon 1060. The animated Y-connector icon 1092 can be presented similar to the animated Y-connector icon 1090 described herein.

Figure 11A:
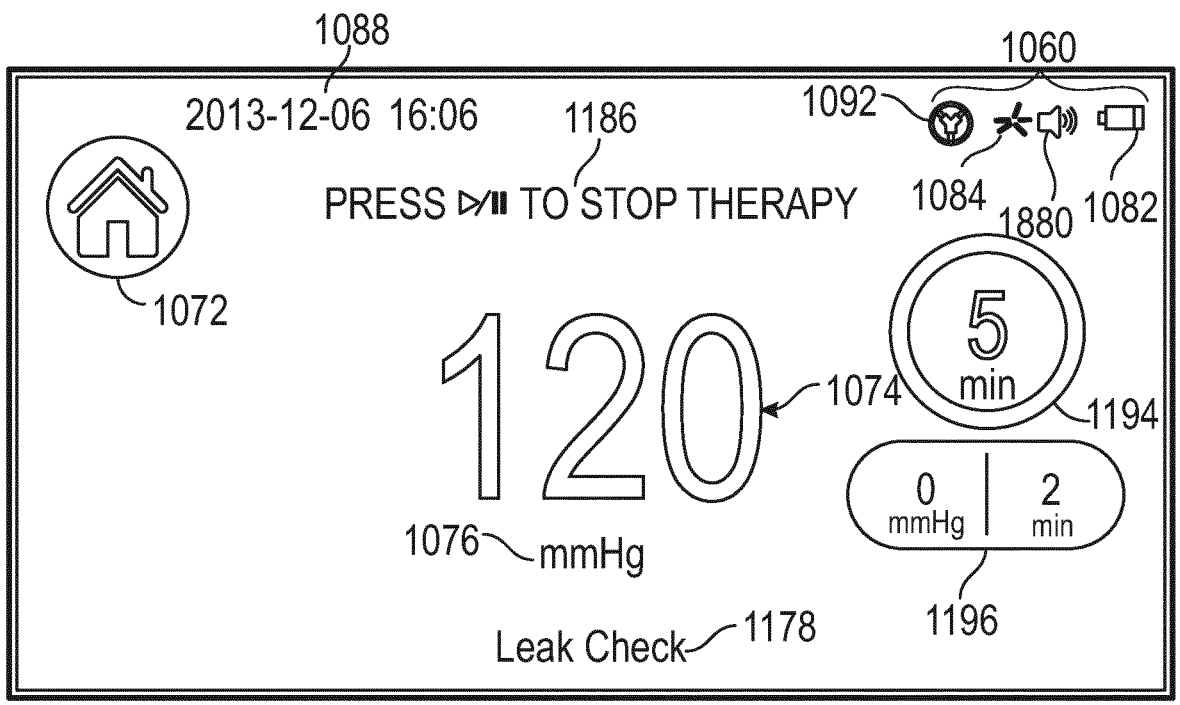
FIGS. 11A-11C illustrate GUIs of a topical negative pressure (TNP) system, according to some embodiments.
Figure 11B:
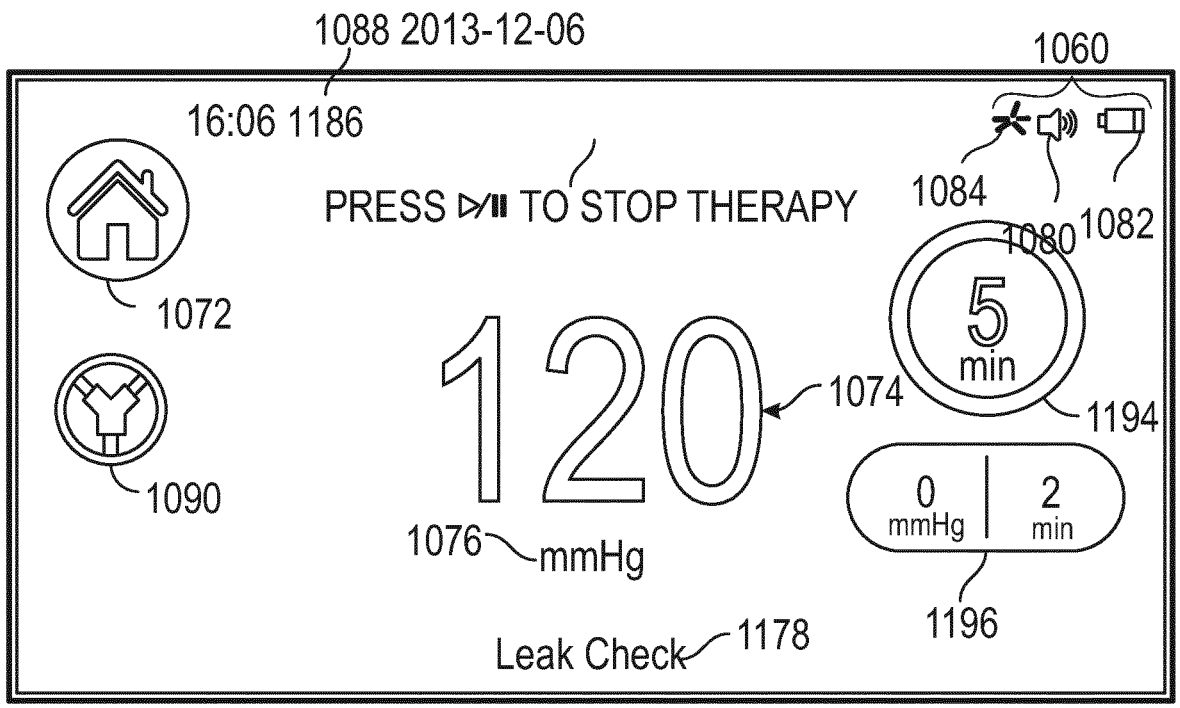
Figure 11C:
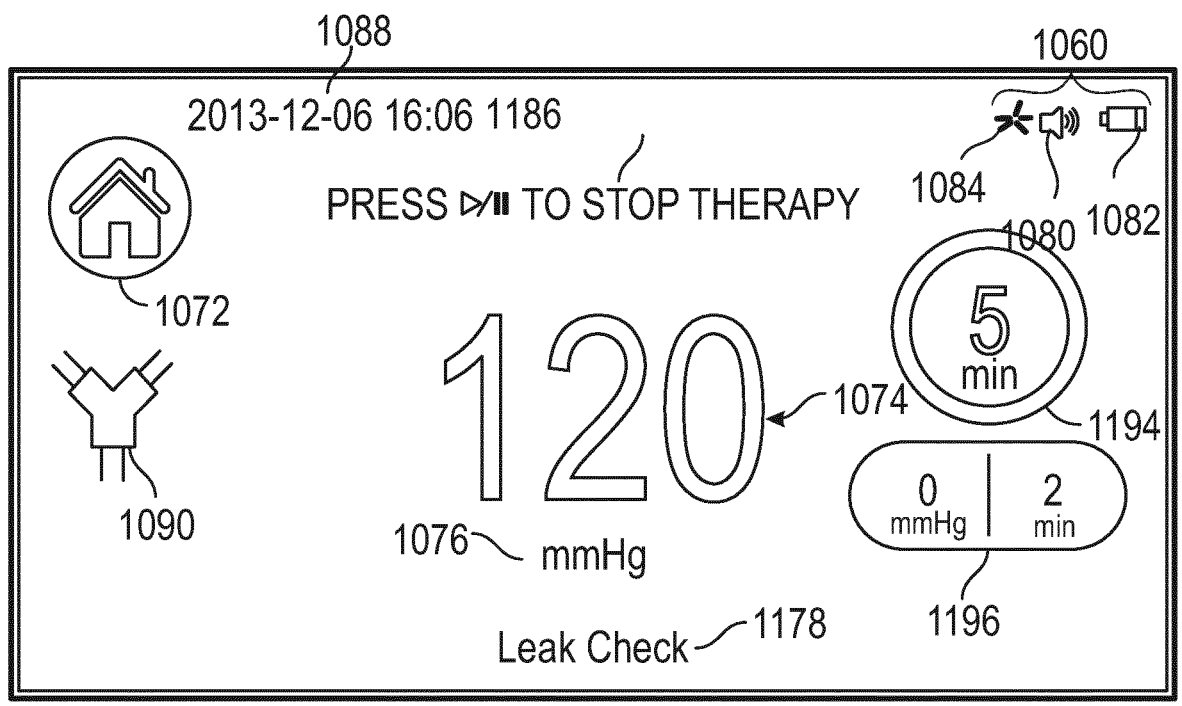

FIGS. 11A-11C illustrate a plurality of GUI screens of a TNP system, according to some embodiments. The illustrated GUI screens can be used with any of the embodiments of TNP systems described herein. Similar to the GUI of FIGS. 10A-10D, the GUI screens can be displayed on the screen 206, which can be configured as a touchscreen interface. FIG. 11A illustrates therapy delivery GUI according to some embodiments. The GUI can be displayed after the user has selected desired therapy settings on a home screen and has initiated therapy, such as by pressing button the 212b. As is illustrated, intermittent therapy is being delivered to a wound. Label 1074 and timer 1194, respectively, indicate that negative pressure of −120 mmHg is being delivered to the wound for 5 minutes. Timer 1194 can be configured to show the remaining amount of time, for example, as a number (e.g., "5 min"), as a relative amount (e.g., by adjusting the fill of the circle), and a combination of the two. Label 1076 can indicate that 0 mmHg (or atmospheric pressure) is scheduled to be delivered to the wound for duration of 2 minutes upon expiration of the time period (e.g., 5 minutes) for delivering the first amount of negative pressure (e.g., −120 mmHg). Message 1178 ("Leak Check") can indicate that the pump assembly 230 is performing a leak check. As is further explained below, the pump assembly 230 can perform a leak check when it initiates delivery of negative pressure therapy to determine if the fluid flow path is sufficiently free of leaks (e.g., is properly sealed). Once it has been determined that no significant leaks are present, message 1178 can indicate this fact to the user, such as by displaying the message "Seal Achieved." Menu item 1072 can be configured to return to a therapy settings screen (or home screen). Additional or alternative controls, indicators, messages, icons, and the like can be used.

The pump assembly 230 can perform a leak check test, which may result in detection of a leak or low vacuum. For example, if at any point during a time period that follows initiation of therapy, such as 45 seconds or any other suitable duration after therapy has been started, the short tachometer average rate falls below the leak threshold, the leak check test has passed and suitable seal is deemed to have been achieved. That is, if pressure at the wound has reached the desired setpoint within the period of time and the flow rate (as indicated by a short tachometer average or any other suitable metric) does not satisfy or exceed the leak threshold, it can be determined that the fluid flow path is suitably sealed and no significant leaks are present (e.g., the dressing has been properly placed and proper connections between pump assembly, canister, and dressing have been made). However, if the short tachometer average remains above the leak threshold at the end of the period of time, a leak is likely to be present, and the pump assembly (e.g., the GUI) can indicate presence of a leak.

In some embodiments, as described herein, a TNP system can include a Y-, W-, or other connector for treating multiple wounds (e.g., two, three, or more wounds) with one pump assembly 230. The GUI of FIG. 11A can indicate that a Y-connect feature has been selected or activated for treatment of multiple wounds. Activating the Y-connect feature can adjust one or more of various thresholds described above. For example, activating a Y-connect feature can decrease sensitivity of blockage detection by increasing the blockage threshold, which is used for blockage detection as explained above. The blockage threshold can be increased by a suitable amount, such as doubled.

As described herein with respect to FIGS. 10A-10D, the pump assembly 150 can include visual, audible, tactile, haptic, or other types of indicators or alarms configured to signal to the user various operating conditions. For example, in the illustrated embodiment, the GUI includes an animated Y-connector status icon 1092, which can have any of the features described above with respect to FIGS. 10A-10D. FIGS. 11B and 11C illustrate example of animated Y-connector icon 1090, which can be presented in addition or alternatively to the animated Y-connector status icon 1092. However, additional or alternative controls, indicators, messages, icons, and the like can be used.

TERMINOLOGY

Depending on the embodiment, certain operations, acts, events, or functions of any of the processes described herein can be performed in a different sequence, can be added, merged, or left out altogether (such as not all are necessary for the practice of the processes). Moreover, in certain embodiments, operations, acts, functions, or events can be performed concurrently, such as through multi-threaded processing, interrupt processing, or multiple processors or processor cores or on other parallel architectures, rather than sequentially.

The processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data repositories shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Any of the embodiments described herein can be used with a canister or without a canister. Any of the dressing embodiments described herein can absorb and store wound exudate.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy apparatus comprising:
 a negative pressure source configured to couple via a plurality of fluid flow paths to a plurality of wounds covered by a plurality of wound dressings and provide negative pressure to the plurality of wounds, the plurality of fluid flow paths comprising:
  a first fluid flow path configured to fluidically connect a first wound dressing of the plurality of wound dressings to a first inlet configured to be in fluid communication with the negative pressure source, the first fluid flow path including a first aperture configured to admit fluid external to the first fluid flow path into the first fluid flow path, wherein the first aperture is associated with a first expected leak rate corresponding to a flow of fluid admitted into the first fluid flow path via the first aperture,
  a second fluid flow path configured to fluidically connect a second wound dressing of the plurality of wound dressings to a second inlet configured to be in fluid communication with the negative pressure source, the second fluid flow path including a second aperture configured to admit fluid external to the second fluid flow path into the second fluid flow path, wherein the second aperture is associated with a second expected leak rate corresponding to a flow of fluid admitted into the second fluid flow path via the second aperture, wherein the second expected leak rate is different than the first expected leak rate, and
a controller configured to operate the negative pressure source, the controller further configured to:
  determine a total rate of flow in the plurality of fluid flow paths;
  detect a presence of at least one operating condition based at least in part on the total rate of flow and at least one of the first expected leak rate or the second expected leak rate, the at least one operating condition comprising one or more of a blockage condition, a system blocked condition, or a normal operating condition; and
  provide indication of the at least one operating condition,
wherein the controller is further configured to:
  based at least in part on a determination that the total rate of flow does not satisfy any of a first, a second, or a third flow thresholds, provide an indication that the system blocked condition exists or an indication that the blockage condition exists in each of the plurality of fluid flow paths, the first flow threshold corresponding to the first expected leak rate, the second flow threshold corresponding to the second expected leak rate, the third flow threshold corresponding to an aggregation of the first expected leak rate and the second expected leak rate, the third flow threshold corresponding to higher flow than the first and second flow thresholds, and the second flow threshold corresponding to higher flow than the first flow threshold;
  based at least in part on a determination that the total rate of flow satisfies the first flow threshold and does not satisfy the second threshold, provide an indication that the blockage condition exists in the second fluid flow path;
  based at least in part on a determination that the total rate of flow satisfies the second flow threshold and does not satisfy the third flow threshold, provide an indication that the blockage condition exists in the first fluid flow path; and
  based at least in part on a determination that the total rate of flow satisfies the third flow threshold, provide an indication that the normal operation condition exists.

2. The apparatus of claim 1, wherein the first expected leak rate corresponds to a rate of flow in the first fluid path under the normal operation condition, and wherein the expected second leak rate corresponds to a rate of flow in the second fluid path under the normal operation condition.

3. The apparatus of claim 1, further comprising an electronic display, wherein the controller is further configured to provide on the electronic display a graphical representation of a rate of flow in at least one of the plurality of fluid flow paths.

4. The apparatus of claim 3, wherein the graphical representation comprises a graphical representation of a gauge.

5. The apparatus of claim 1, wherein the negative pressure source comprises a vacuum pump including a motor, and the controller is configured to determine the rate of flow in the plurality of fluid flow paths by measuring a speed of the motor.

6. The apparatus of claim 5, further comprising a tachometer configured to measure the speed of the motor.

7. The apparatus of claim 5, wherein the controller is further configured to measure a first plurality of motor speeds during a first period of time and determine an average of the first plurality of motor speeds, the average being indicative of the total rate of flow.

8. The apparatus of claim 1, further comprising a canister configured to collect fluid aspirated from the plurality of wounds.

9. The apparatus of claim 1, further comprising a connector configured to connect the negative pressure source to the plurality of fluid flow paths, the connector comprising:
  a plurality of dressing conduit attachment portions fluidically connected to a negative pressure attachment portion via a joint, the plurality of dressing conduit attachment portions comprising:
    a first dressing conduit attachment portion including a first shaft extending away from the joint and including the first inlet distal the joint, the first inlet configured to fluidically connect the first fluid flow path to the negative pressure source, and
    a second dressing conduit attachment portion including a second shaft extending away from the joint and including the second inlet distal the joint, the second inlet configured to fluidically connect the second fluid flow path to the negative pressure source, and
  the negative pressure attachment portion including a third shaft extending away from the joint and including a third inlet distal the joint, the third inlet configured to fluidically connect to an inlet of the negative pressure source.

10. The apparatus of claim 9, further comprising a third fluid flow path configured to fluidically connect a third wound dressing to a fourth inlet configured to be in fluid communication with the negative pressure source, the third fluid flow path including a third aperture configured to admit fluid external to the third fluid flow path into the third fluid flow path, wherein the third aperture is associated with a third expected leak rate corresponding to a flow of fluid admitted into the third fluid flow path via the third aperture, and wherein the third expected leak rate is different from the first expected leak rate and the second expected leak rate.

11. The apparatus of claim 10, wherein the plurality of dressing conduit attachment portions configured to connect the negative pressure source to the plurality of fluid flow paths further comprises a third dressing conduit attachment portion including a fourth shaft extending away from the joint and including the fourth inlet distal the joint, the fourth inlet configured to fluidically connect the third fluid flow path to the negative pressure source.

12. The apparatus of claim 1, wherein the controller is further configured to generate one or more graphical user interfaces (GUIs).

13. The apparatus of claim 1, wherein the total rate of flow comprises the total rate of flow in the plurality of fluid flow paths at steady state operation.

14. The apparatus of claim 1, wherein the controller is configured to determine the total rate of flow without using a flow sensor.

15. The apparatus of claim 1, wherein the controller is configured to detect the presence of the at least one operating condition based at least in part on the total rate of flow, the first expected leak rate, and the second expected leak rate.

* * * * *